(12) United States Patent
Topolancik et al.

(10) Patent No.: US 11,143,618 B2
(45) Date of Patent: Oct. 12, 2021

(54) FABRICATION OF TUNNELING JUNCTIONS WITH NANOPORES FOR MOLECULAR RECOGNITION

(71) Applicant: Roche Sequencing Solutions, Inc., Pleasanton, CA (US)

(72) Inventors: Juraj Topolancik, Redwood City, CA (US); Zsolt Majzik, Dublin, CA (US); Flint Mitchell, Menlo Park, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 314 days.

(21) Appl. No.: 16/376,824

(22) Filed: Apr. 5, 2019

(65) Prior Publication Data

US 2019/0310241 A1 Oct. 10, 2019

Related U.S. Application Data

(60) Provisional application No. 62/654,894, filed on Apr. 9, 2018.

(51) Int. Cl.
*G01N 27/447* (2006.01)
*G01N 33/487* (2006.01)
*C12Q 1/6869* (2018.01)
*G01N 27/327* (2006.01)

(52) U.S. Cl.
CPC ..... *G01N 27/44791* (2013.01); *C12Q 1/6869* (2013.01); *G01N 27/3278* (2013.01); *G01N 33/48721* (2013.01)

(58) Field of Classification Search
CPC ....... G01N 27/44791; G01N 33/48721; G01N 27/3278; C12Q 1/6869; C12Q 1/6825; B81B 2201/0214; B81B 2203/04; B81C 1/00087
See application file for complete search history.

(56) References Cited

U.S. PATENT DOCUMENTS

| 7,250,115 B2* | 7/2007 | Barth | B82Y 5/00 |
| | | | 204/192.34 |
| 7,678,562 B2* | 3/2010 | Ling | C12Q 1/6869 |
| | | | 435/283.1 |
| 9,449,891 B1* | 9/2016 | Wang | B81B 3/0094 |
| 10,190,159 B2 | 1/2019 | Astier | |
| 2017/0003245 A1* | 1/2017 | Lindsay | G01N 27/3276 |
| 2017/0043339 A1* | 2/2017 | Astier | B81C 1/00063 |
| 2017/0307587 A1* | 10/2017 | Yanagi | G01N 27/3278 |
| 2018/0031523 A1 | 2/2018 | Astier | |

OTHER PUBLICATIONS

Yuan et al, Solid-State Nanopore, 2018, Nanoscale Research Letters, 13:56, pp. 1-10 (Year: 2018).*
Dekker et al, Solid-state nanopores, 2017, Nature Nanotechnology, 209-215 (Year: 2017).*
Kim, Y. et al.; "Noise Characteristics of Charge Tunneling via Localized States in Metal-Molecule-Metal Junctions"; *ACSNANO*; vol. 4, No. 8; 2010; pp. 4426-4430.
Vasudevan, S. et al.; "Using Room Temperature Current Noise To Characterize Single Molecular Spectra"; *ACSNANO*; vol. 8, No. 3; 2014; pp. 2111-2117.
Zhang, B. et al.; "Observation of giant conductance fluctuations in a protein"; *Nano Futures I*; 2017; 035002; 15 pages.

* cited by examiner

*Primary Examiner* — Narayan K Bhat
(74) *Attorney, Agent, or Firm* — Kilpatrick Townsend and Stockton LLP

(57) ABSTRACT

Embodiments of the present technology may allow for improved and more reliable tunneling junctions and methods of fabricating the tunneling junctions. Electrical shorting issues may be reduced by depositing electrodes without a sharp sidewall and corner but instead with a sloping or curved sidewall. Layers deposited on top of the electrode layer may then be able to adequately cover the underlying electrode layer and therefore reduce or prevent shorting. Additionally, two insulating materials may be used as the dielectric layer may reduce the possibility of incomplete coverage and the possibility of flaking. Furthermore, the electrodes may be tapered from the contact area to the junction area to provide a thin electrode where the hole is to be patterned, while the thicker contact area reduces sheet resistance. The electrode may also be patterned to be wider at the contact area and narrower at the junction area.

10 Claims, 19 Drawing Sheets

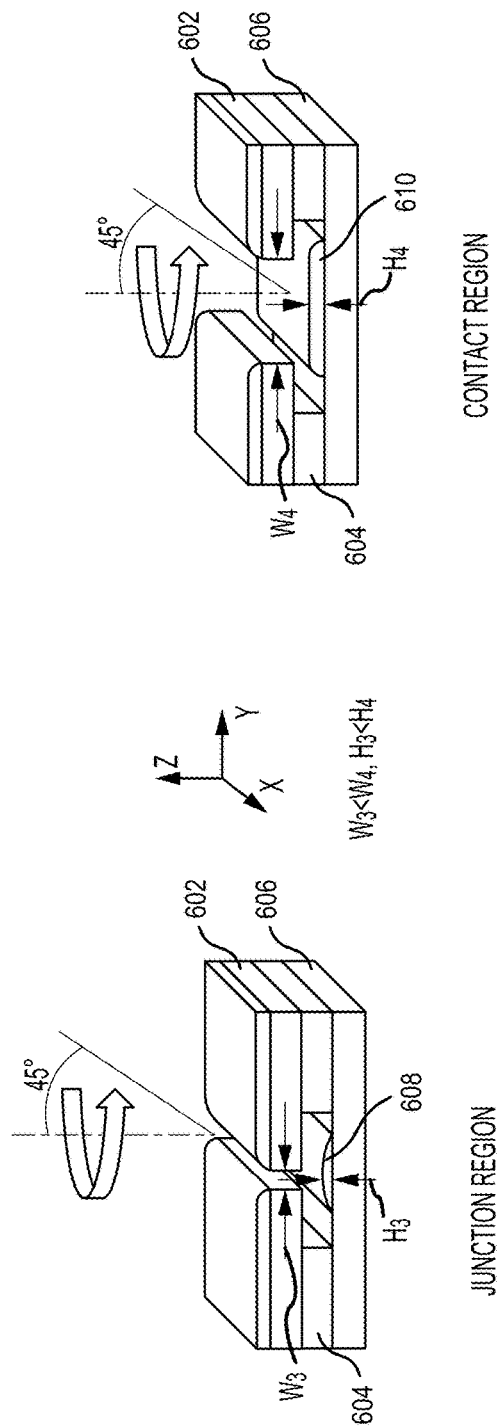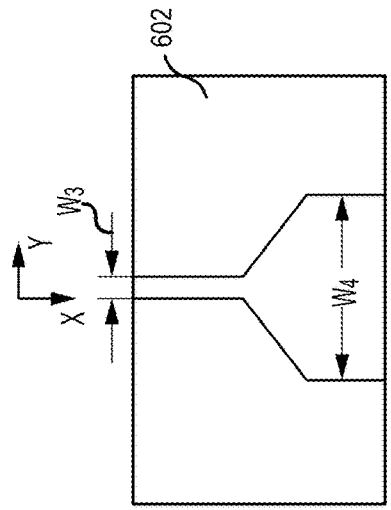
FIG. 6A
FIG. 6B

FABRICATION OF TUNNELING JUNCTIONS WITH NANOPORES FOR MOLECULAR RECOGNITION

CROSS-REFERENCE TO RELATED APPLICATIONS

This application claims priority to U.S. Provisional Application No. 62/654,894, filed Apr. 9, 2018, the contents of which are hereby incorporated by reference in its entirety for any and all purposes.

FIELD

This application relates to systems to analyze molecules using tunnel junctions, methods to make such systems, and methods to use such systems. Such analysis of molecules can include sequencing biological polymers, such as nucleic acids.

BACKGROUND

Nanopores have the ability to detect single molecules, which is promising technology in the field of chemical and biological detection. For example, nanopores may be used for nucleic acid sequencing. Solid-state nanopores are one type used for rapidly bio-sensing a molecule sensing technique. In some cases, solid-state nanopores form a channel in an ionic liquid between two electrodes. The two electrodes may not be part of the nanopore itself but may be positioned in the ionic liquid. As a molecule passes though the nanopore channel, the current and other electrical characteristics through the channel change. These electrical characteristics can provide information on the molecule, but fabrication issues may make identifying individual nucleotides in a nucleic acid molecule difficult.

Nanopore devices use tunneling recognition. Tunneling recognition is based on placing a nucleotide of a nucleic acid between electrodes, which may be in the nanopore device itself. The orbitals of the nucleotide will allow electrons to transfer from one electrode to the other, creating a tunneling current. Dimensions and other properties of solid-state nanopores may be difficult to adapt to a mass production process. To sequence nucleic acid molecules with ionic current, nanopore dimensions may need to be on the order of nanometers, e.g., less than 2 nm. Creating a channel of this size may require precise and expensive techniques. However, reducing dimensions of the nanopore may result in incomplete or poor wetting needed for the nanopore to function as a sensing device. Improvements in the design and manufacturability of nanopore-containing devices used in chemical and biological detection and processes involving the devices are still needed. Design and manufacturability improvements should not come at the expense of accurate and precise analysis. These and other issues are addressed by the technology described in this document.

BRIEF SUMMARY

For tunneling junctions, a thin dielectric between two metal electrodes is desired. A tunneling junction may include a hole through the electrodes and the dielectric. Fabricating these tunneling junctions, with dimension on the order of nanometers, is difficult. Electrodes may be patterned perpendicular to each other for alignment purposes. However, the perpendicular alignment of electrodes may result in shorts resulting from the sharp sidewalls of the electrodes and the thin dielectrics covering the sharp sidewalls. Additionally, a thin dielectric may itself be a poor barrier for shorting. Metal from an electrode may become embedded in the dielectric. The metal along with dielectric material may flake off, creating a void and possibility for a short. Furthermore, electrode thickness may also present a challenge. Because a hole may be patterned in the electrode, a thin electrode may make patterning easier. However, a thin electrode also results in increased sheet resistance.

Embodiments of the present technology may allow for improved and more reliable tunneling junctions and methods of fabricating the tunneling junctions. Electrical shorting issues may be reduced by depositing electrodes without a sharp sidewall and corner, but instead with a sloping or curved sidewall. Layers deposited on top of the electrode layer may then be able to adequately cover the underlying electrode layer and therefore reduce or prevent shorting. Additionally, two insulating materials may be used as the dielectric layer, thereby reducing the possibility of incomplete coverage and the possibility of flaking. Furthermore, the electrodes may be tapered from the contact area to the junction area to provide a thin electrode where the hole is to be patterned, while the thicker contact area reduces sheet resistance. The electrode may also be patterned to be wider at the contact area and narrower at the junction area.

A better understanding of the nature and advantages of embodiments of the present invention may be gained with reference to the following detailed description and the accompanying drawings.

BRIEF DESCRIPTION OF THE DRAWINGS

FIG. 6A shows using different sized openings of resist to deposit the metal layer according to embodiments of the present invention.

FIG. 6B shows a top view of the resist opening according to embodiments of the present invention.

TERMS

Figure 1A:
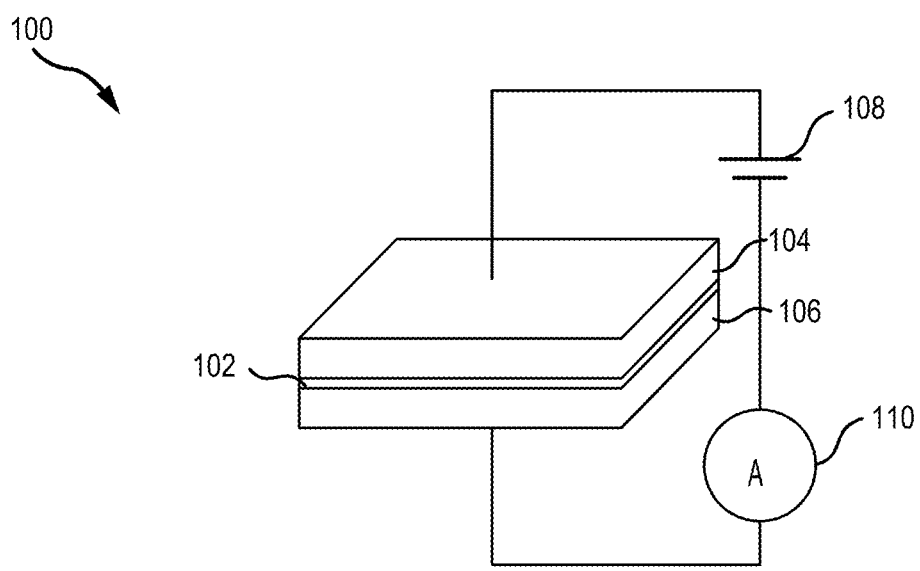
FIG. 1A shows a metal-insulator-metal junction according to embodiments of the present invention.

The term "contacting" may refer to bringing one object in proximity to another object such that electrons may tunnel from one object through the other object. At a subatomic level, two objects may never physically touch each other as repulsive forces from electron clouds in the objects may prevent the objects from coming into closer proximity.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

The term "oscillate" may refer to the motion of an object in a fluid as a result of Brownian motion or other forces. An object may oscillate without active intervention by a person or a machine. In some cases, an object may oscillate as a result of an applied electric field or a pressure-driven flow.

Directional terms such as "above" or "on top of" for semiconductor processing layers and steps may use a reference frame where these terms designate a position farther away from a plane defined by a surface of the substrate. The "bottom" may be the underside of a substrate or toward the underside of the substrate. One of skill would understand that even if a substrate is processed upside-down, the "bottom" of a layer may still refer to a side of the layer closest to the underside or non-processed side of a substrate.

The term "electrical characteristic" may be understood to refer to any property related to an electrical circuit. Electrical characteristic may refer to voltage, current, resistance, impedance, inductance, or capacitance, and time variations thereof (e.g., current frequency).

DETAILED DESCRIPTION

Conventional nanopore-based devices currently on the market may contain protein nanopores inserted in metastable lipid bilayers. The lipid bilayers may be fragile and may undermine the stability of the devices. Solid-state atomic scale nanopore layers may be less fragile than protein nanopores and have the potential for improved manufacturability. Possible methods involving these devices include confining nucleic acid molecules in a gap of 2 nm or less between electrodes and recognizing nucleotides and nucleotide sequences using electrons that tunnel through the electrodes and the nucleic acid molecule. Conventional solid-state methods may be difficult to adapt to reliable mass production of nanopores, nanopore-containing devices, and analytical instruments. Devices made by conventional methods may be electrically shorted even before nanopores are patterned. After patterning, the remaining devices may degrade rapidly during operation.

Embodiments of the present technology may allow for improved and more reliable tunneling junctions and methods of fabricating the tunneling junctions. Electrical shorting issues may be reduced by depositing electrodes without a sharp sidewall and corner, but instead with a sloping or curved sidewall. Layers deposited on top of the electrode layer may then be able to adequately cover the underlying electrode layer and therefore reduce or prevent shorting. Additionally, two insulating materials may be used as the dielectric layer, thereby reducing the possibility of incomplete coverage and the possibility of flaking. Furthermore, the electrodes may be tapered from the contact area to the junction area to provide a thin electrode where the hole is to be patterned, while the thicker contact area reduces sheet resistance. The electrode may also be patterned to be wider at the contact area and narrower at the junction area.

I. Nanopores Using Tunneling

FIG. 1A shows a simple device 100 that may be used for tunneling recognition of molecules. An insulating layer 102 separates metal 104 and metal 106. Metal 104 and metal 106 may be electrodes. A voltage may be applied to metal 104 and metal 106 from power supply 108. When a molecule contacts both metal 104 and 106, electrons may tunnel through the nucleic acid molecule from one electrode to the other, generating a current. The current may be measured by meter 110. The molecule may oscillate, and the measured current may have an amplitude and frequency. The amplitude and frequency may be variable. The characteristics of the current may aid in identifying a particular molecule or portion of the molecule. The electrical characteristics may serve almost as a fingerprint in identifying the molecule or portion of the molecule.

Figure 1C:
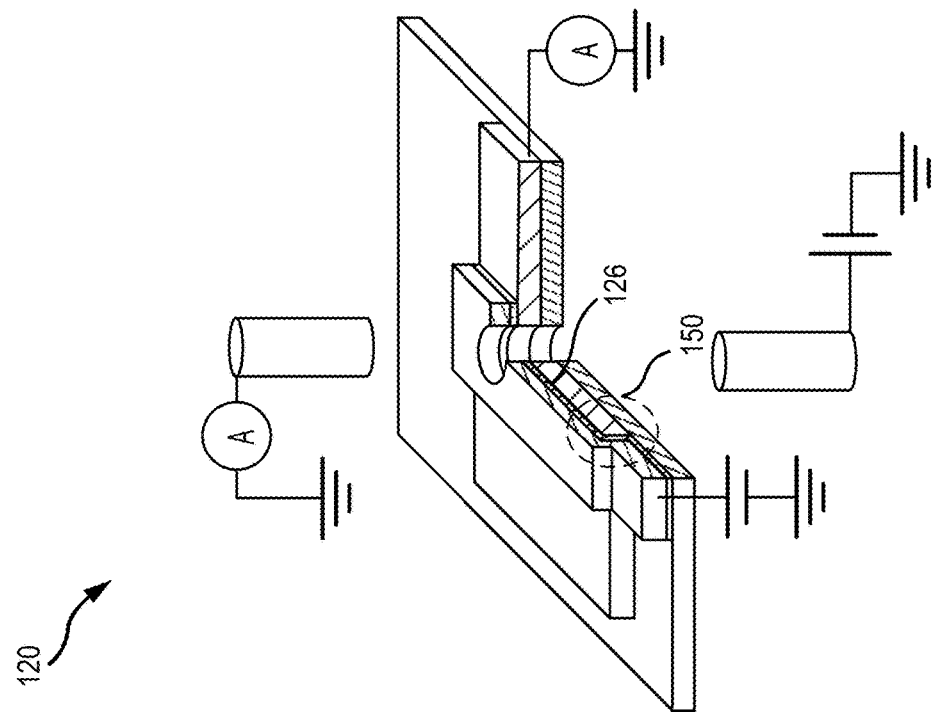
FIGS. 1B and 1C show views of a solid-state nanopore device according to embodiments of the present invention.
Figure 1B:
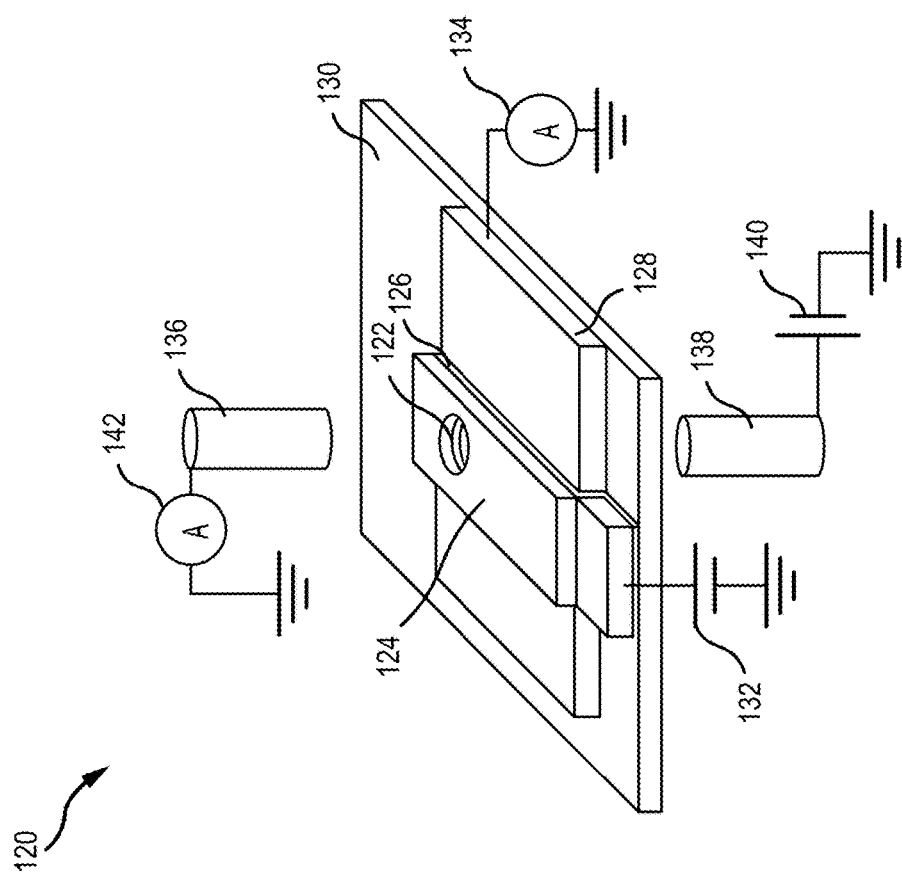

FIG. 1B shows a solid-state nanopore device 120 fabricated by conventional techniques. Device 120 has an aperture 122. Aperture 122 may permit only one molecule to pass through at a time, which may simplify recognition of the molecule. Aperture 122 may be formed in a top metal electrode 124, an insulating layer 126, and a bottom metal electrode 128. Bottom metal electrode 128 may be on a substrate 130. Top metal electrode 124 may be connected to a power supply 132. Bottom metal electrode 128 may be connected to an electrical meter 134. A top electrode 136 and a bottom electrode 138 may produce an electric field to help drive a molecule into aperture 122. Bottom electrode 138 may be connected to a power supply 140. Top electrode 136 may be connected to an electrical meter 142.

FIG. 1C shows a cutaway view of device 120. The effect of the sharp sidewalls of the metal electrodes is more apparent in region 150. The layers on top of the step formed by bottom metal electrode 128 can be seen. Insulating layer 126 may have a thickness on the order of nanometers (e.g., 1-2 nm) on the top surface of bottom metal electrode 128. Insulating layer 126 in the diagram shows conformal coverage of bottom metal electrode 128. However, the insulator may not conformally cover the step in practice. The sidewall coverage of the bottom metal electrode 128 may be thinner than the coverage on the top surface of bottom metal electrode 128. The thin coverage may be an area where shorting between top metal electrode 124 and bottom metal electrode 128 is more likely.

Figure 1D:
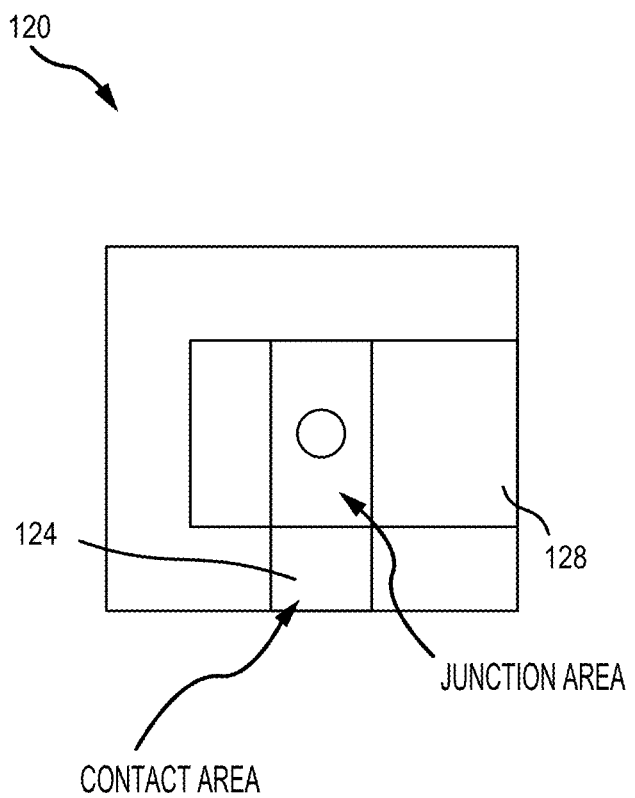
FIG. 1D illustrates areas of a solid-state nanopore device according to embodiments of the present invention.

FIG. 1D shows a two-dimensional view of device 120. The figure also shows that the junction area is the area where top metal electrode 124 and bottom metal electrode 128 overlap. The contact area is the area where the electrodes do not overlap.

II. Techniques for Improving Reliability and Manufacturability

Three techniques are described to improve reliability and manufacturability of nanopore devices. As mentioned above, a potential weakness in reliability and manufacturability of the nanopore device in FIGS. 1B and 1C may be the sharp sidewalls of the electrode and the thin insulating layer coverage between the electrodes. First, electrodes with sloping sidewalls may be deposited so that the coverage of the insulating layer over the electrode may be thicker, thereby reducing the possibility of shorting. Second, the insulating layer may include multiple insulator layers may prevent voids from forming and creating shorts. Third, the electrode layer may be tapered in two dimensions so that the electrode is easier to manufacture and will not have too high a sheet resistance for normal operation.

A. Electrodes with Sloping Sidewalls

The possibility of shorting may be reduced by forming an electrode without a vertical or substantially vertical sidewall. The electrode may have a sloping sidewall or may be curved or rounded. The structure of the electrodes is introduced here. The process used to deposit the electrodes is discussed later.

Figure 2:
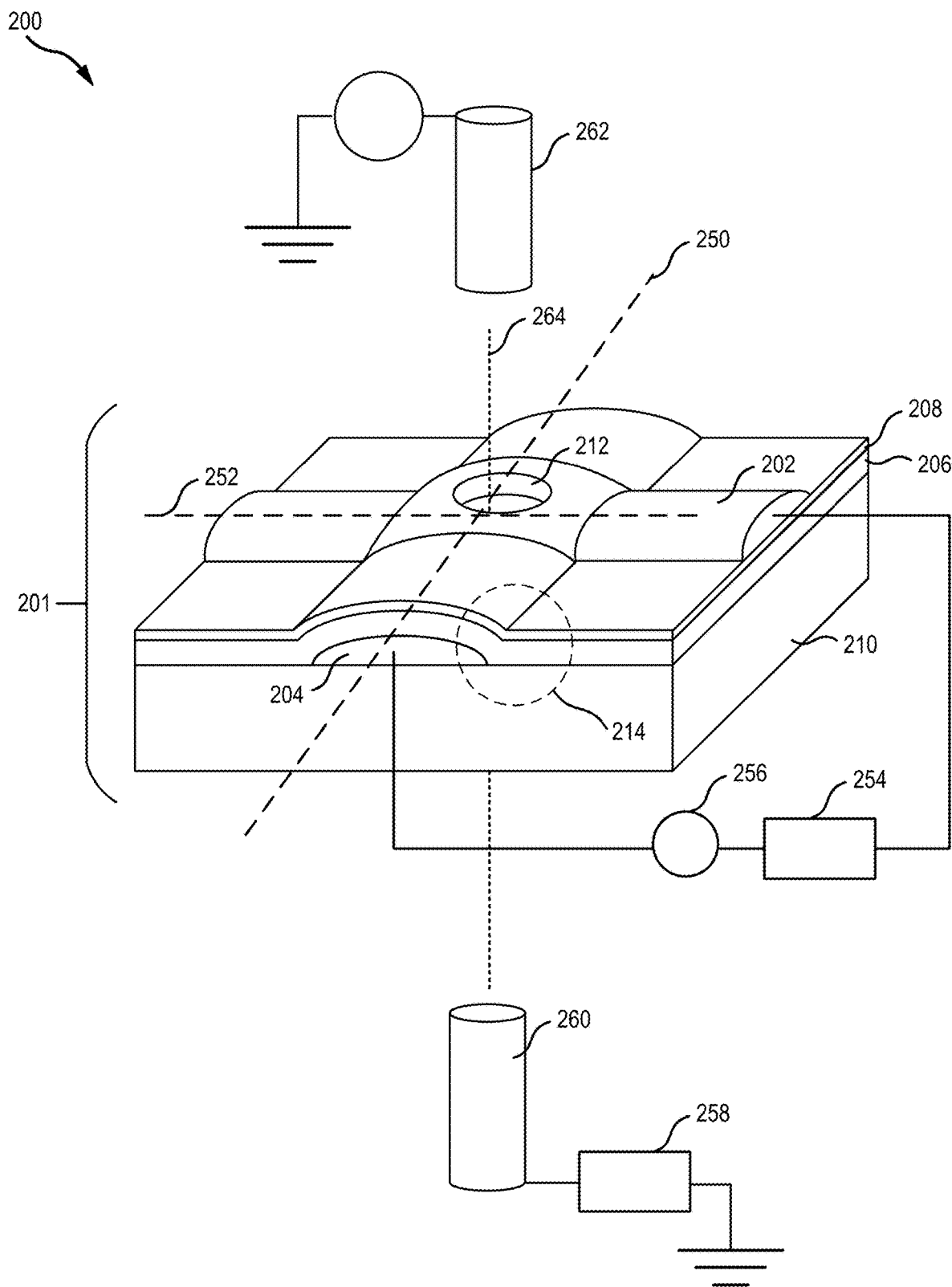
FIG. 2 shows a diagram of a system 200 with a device 201 without electrodes with vertical sidewalls according to embodiments of the present invention.

FIG. 2 shows a diagram of a system 200 with a device 201 without electrodes with vertical sidewalls. A top metal electrode 202 is above bottom metal electrode 204. A first insulator layer 206 and a second insulator layer 208 separate top metal electrode 202 and bottom metal electrode 204. Bottom metal electrode 204 is on top of substrate 210. An aperture 212 may be through top metal electrode 202, second insulator layer 208, first insulator layer 206, bottom metal electrode 204, and substrate 210. As can be seen in area 214, no vertical sidewall of bottom metal electrode 204 is present to be covered by first insulator layer 206. Instead, bottom metal electrode 204 has a gradual curve or slope, which can be covered conformally by an insulator layer more easily than a vertical sidewall.

Top metal electrode 202 may also have sloped sidewalls. Sloped sidewalls may ensure suitable coverage for the insulator layer covering this electrode. With sloped sidewalls, an insulator layer deposited above top metal electrode 202 may avoid formation of voids and seams. During operation of the nanopore device, the molecule to be analyzed may be in a liquid medium. Voids and seams may allow liquids to penetrate to the electrode, which may allow unwanted electrical paths from an ionic liquid to top metal electrode 202. In other words, sloping sidewalls with top metal electrode 202 may aid isolation of top metal electrode from liquids.

B. Multiple Insulator Layers

A thin insulating layer is desired between the electrodes so that when the molecule contacts both electrodes, the tunneling current through the molecule can be through a small enough portion of the molecule to facilitate analysis. For example, if the molecule to be analyzed is a DNA molecule, the insulating layer should be thin so that when the DNA molecule contacts both electrodes, the current passes through only a single nucleotide. However, a thin insulating layer provides less of a barrier between the electrodes than a thick insulating layer. At edges of the bottom electrode, particles of metal may be present. The metal particles may have flaked off the edge of the electrode during or shortly after depositing the electrode. If a thin insulating layer is used to cover these metal particles at the edges of the bottom electrode, the thin insulating layer may be removed or etched away before another electrode is deposited. These metal particles may then no longer be covered by an insulating layer when another electrode is deposited onto the bottom electrode. The bottom electrode and the top electrode may contact and create a short. The metal particles present at edges of the electrode may also be more prevalent with a geometry with vertical sidewalls.

Figure 3A:
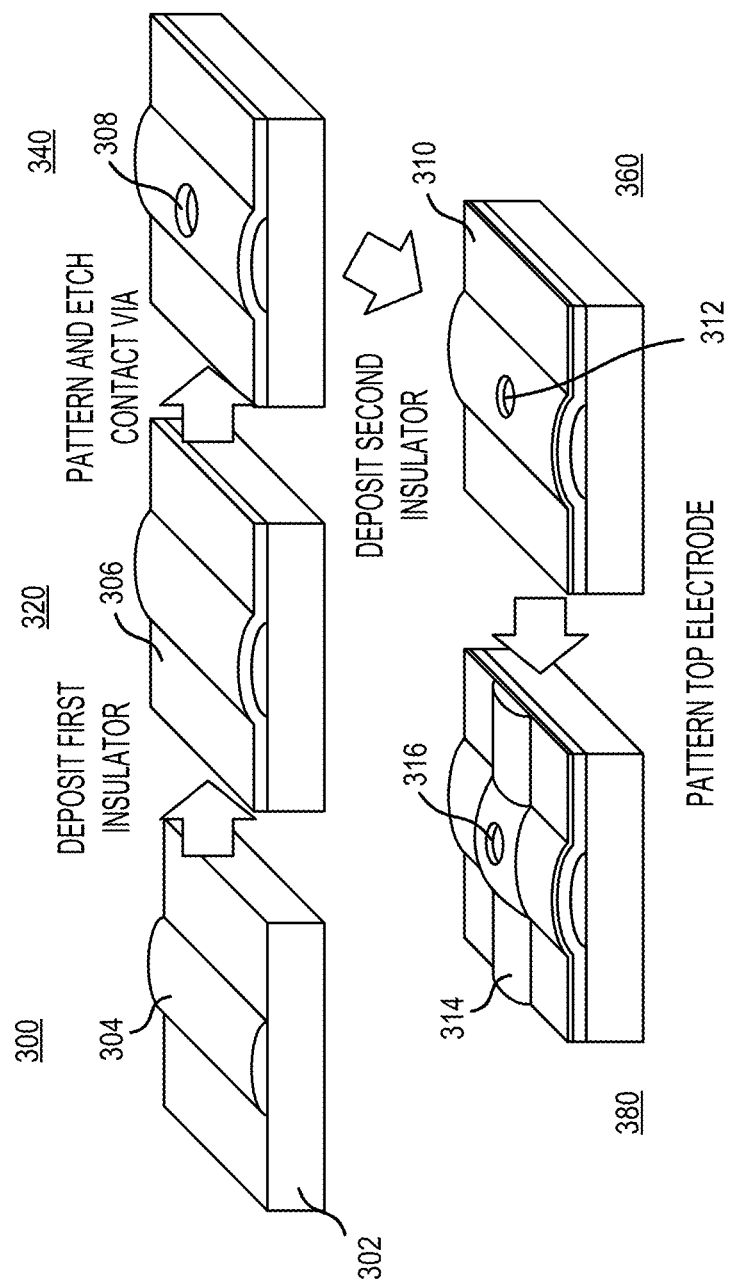
FIG. 3A shows a process flow for depositing an insulator layer according to embodiments of the present invention.

FIG. 3A illustrates a process flow that may maintain the integrity of a thin insulating layer between the electrodes. At step 300, a substrate 302 starts with a metal electrode 304 on top. At step 320, the first insulator material is deposited to form first insulator layer 306.

Figure 3B:
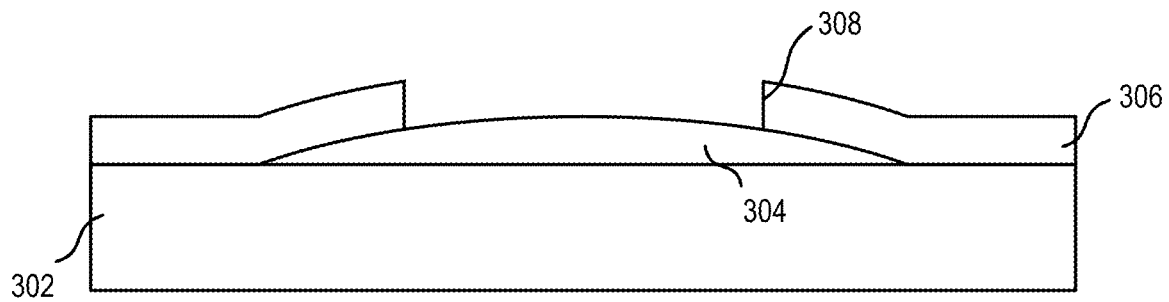
FIGS. 3B, 3C, and 3D show cross sections during the process for forming a nanopore according to embodiments of the present invention.

At step 340, a contact via 308 may be etched in first insulator layer 306. The bottom of contact via 308 may be an exposed portion of metal electrode 304. FIG. 3B shows a cross section through contact via 308 at step 340.

Figure 3C:
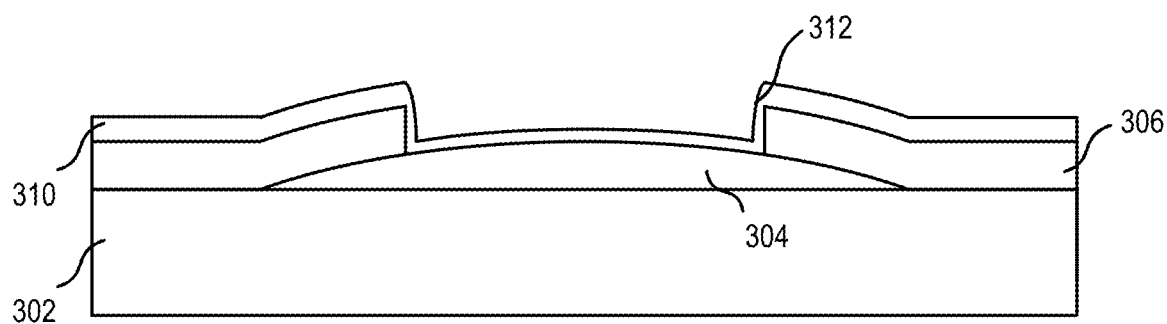

At step 360, a second insulator material may be deposited to form a second insulator layer 310. Second insulator layer 310 may include the material used as the junction insulator. The second insulator material may be deposited on surfaces defining contact via 308, including on the exposed portion of metal electrode 304 and on portions of first insulator layer 306. Contact via 308 is also covered by second insulator layer 310 to form a second via 312. Second via 312 may have a smaller diameter than contact via 308, as contact via 308 reduced by the thickness of the deposited second insulator. The bottom of second via 312 is a portion of second insulator layer 310. FIG. 3C shows a cross section through second via 312 at step 360.

Figure 3D:
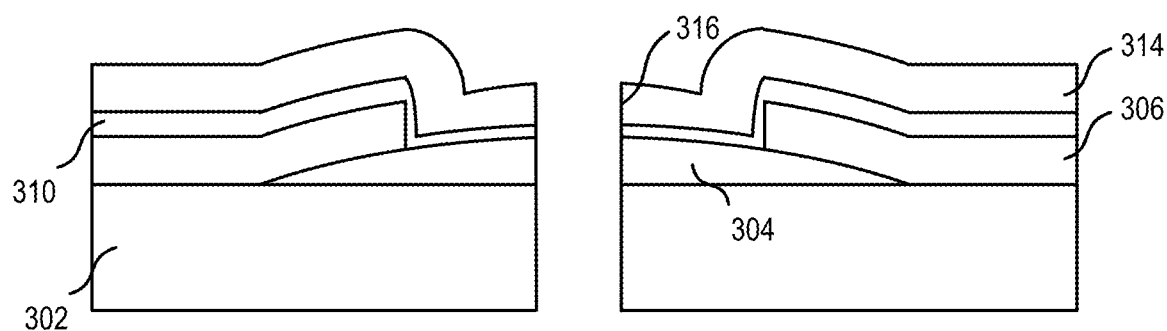

At step 380, a metal material may be deposited to form top electrode 314. Also at step 380, a hole 316 may be etched through all the layers, including top electrode 314, second insulator layer 310, first insulator layer 306, metal electrode 304, and substrate 302. The size of hole 316 may be smaller than both contact via 308 and second via 312. FIG. 3D shows a cross section through hole 316. Second insulator layer 310 separates metal electrode 304 from top electrode 314 and forms the width of the tunneling junction.

The two insulator layers in FIG. 3 may allow for better coverage of metal electrode 304 and may reduce possibility of a short. First insulator layer 306 covers the edge of metal electrode 304, which as a thick insulator layer, may provide adequate coverage of any metal particles that flake off the sides of metal electrode 304. In addition, etching a contact via through first insulator layer 306 may facilitate later etching of the nanopore itself and reduce alignment and processing issues.

C. Tapering from Contact Area to Junction Area

A thinner electrode for a nanopore is desired to make fabrication easier. Etching or otherwise forming a hole is easier through a thin electrode as compared to a thick electrode. A thinner electrode also increases sheet resistance. To some degree, greater sheet resistance is desired so that a change in current or voltage when a molecule contacts the electrodes can be more easily detected. However, increasing the sheet resistance may increase heat and may lead to device failure. To address these issues, the electrode may be tapered in at least two directions from the contact region to the junction region. The structure of the electrodes is described below. The process flow to taper the electrodes is described later.

Figure 4A:
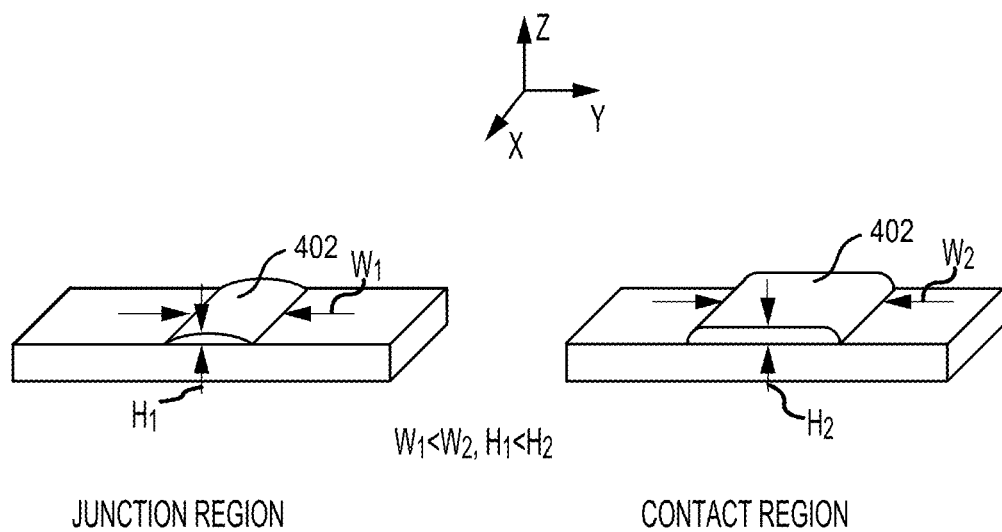
FIGS. 4A and 4B show views of the junction region and the contact region according to embodiments of the present invention.

FIG. 4A shows views of the junction region and the contact region side by side. The junction region may have an electrode 402 with a height $H_1$ and a width $W_1$. The contact region may have the same electrode 402, but with height $H_2$ and width $W_2$. Width $W_2$ may be greater than width $W_1$. Height $H_2$ may be greater than height $H_1$.

Figure 4B:
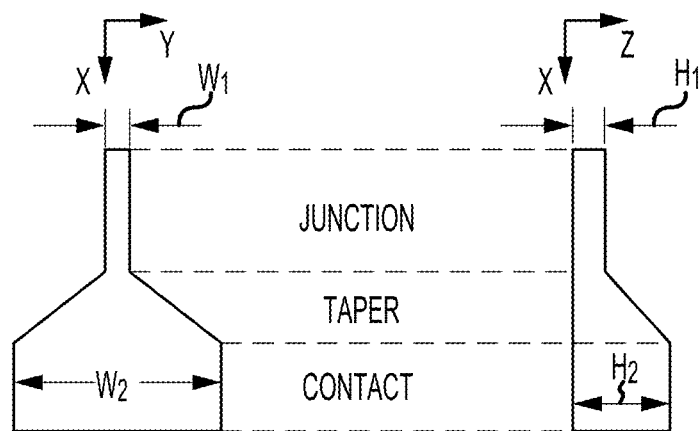

FIG. 4B shows how both the height and width may taper from the contact region to the junction region. The taper may be continuously or monotonically decreasing from width $W_2$ to width $W_1$. The taper may be continuously or monotonically decreasing from $H_2$ to $H_1$. In some embodiments, the taper may be linear. In other embodiments, the taper may follow a curve. In some embodiments, the taper of the width may be symmetric on both sides as in FIG. 4B. In other embodiments, the taper of the width may not be symmetric. For example, one side may be flat while the other side is tapered. With the height, the taper may only be on one side because the bottom of the electrode is fixed by the underlying layer.

Tapering the thickness may allow forming the nanopore through a thin portion of the electrode. Tapering the width will allow for the sheet resistance to be high near the junction region but lower near the contact region.

Embodiments of the present technology may result in a process yield approaching 100% even when the insulating layer is around 2 nm thick. The tunneling currents in the devices may be proportional to the cross-sectional area of the junctions, which is consistent with standard metal-insulator-metal junction models. A method of tapering in at least two directions may be independent from forming electrodes with sloping sidewalls or depositing multiple insulator layers.

III. System

Embodiments may include a system for analyzing a molecule. The system may be similar to system 200 in FIG. 2. The system may include device 201. Device 201 may include a first electrode, such as bottom metal electrode 204. Bottom metal electrode 204 may include a first conductive material. The conductive metal may include a noble metal, which includes, for example, gold, platinum, and palladium. Any metal may be used that has a metal oxide that is chemically stable in the aqueous solution used as the medium for the molecule to be analyzed. Other metals may include transition metals, including period 4 elements (e.g., chromium, nickel, and copper), period 5 elements (e.g., palladium), and period 6 elements (e.g., tantalum). In some embodiments, other metals may include refractory metals (e.g., niobium, molybdenum, tantalum, tungsten, rhenium, titanium, vanadium, chromium, zirconium, hafnium, ruthenium, rhodium, osmium, iridium). Bottom metal electrode 204 may contact a surface of substrate 210. Substrate 210 may be a semiconductor substrate, including a silicon wafer or a silicon-on-insulator wafer.

Bottom metal electrode 204 may have non-vertical sidewalls. One of skill would recognize that perfectly vertical sidewalls are uncommon with semiconductor processing techniques. However, the sidewalls of the bottom metal electrode 204 are intended to be non-vertical, unlike with other semiconductor processing when the sidewalls are intended to be vertical, but processing imperfections result in a non-vertical sidewall. Hence, the sidewalls of the electrode may be more sloping than with normal processing variations. The sidewalls may have a radius of curvature of 0 nm to 1 nm, 1 nm to 2 nm, 2 nm to 5 nm, 5 nm to 10 nm, 10 nm to 20 nm, 20 nm to 25 nm, 25 nm to 50 nm, or greater than 50 nm. A larger radius of curvature may allow for better sidewall coverage. The sidewalls may slope at angles of greater than 0 degrees to 10 degrees, from 10 degrees to 20 degrees, from 20 degrees to 30 degrees, from 30 degrees to 40 degrees, from 40 degrees to 45 degrees, from 45 degrees to 50 degrees, from 50 degrees to 60 degrees, from 60 degrees to 70 degrees, from 70 degrees to 80 degrees, or from 80 degrees to less than 90 degrees. The angle of the slope of a curved sidewall may be measured as the average angle or the angle of a line tangent to the sidewall at half the thickness of the metal electrode. A smaller angle may allow for better sidewall coverage. Bottom metal electrode 204 may be formed by depositing the first conductive material at a non-perpendicular angle while rotating the substrate after forming a resist layer. An example deposition process for the first electrode is described later.

Device 201 may include a second electrode including a second conductive material. The second electrode may be top metal electrode 202. The second conductive material may be the same or different material as the first conductive material. Top metal electrode 202 may have non-vertical sidewalls, similar to the sidewalls for the bottom metal electrode 204. Top metal electrode 202 may be formed by depositing the first conductive material at a non-perpendicular angle while rotating the substrate after forming a resist layer. The deposition process for the second electrode is described later in this document.

The device may include an insulating layer disposed between bottom metal electrode 204 and top metal electrode 202. The insulating layer may include a first insulating material and a second insulating material. In other words, the insulating layer may include two layers of insulating materials. The first insulating material may be first insulator layer 206. The second insulating material may be second insulator layer 208. A first portion of second insulator layer 208 may be disposed between the first insulator layer 206 and top metal electrode 202. A second portion of second insulator layer 208 may be disposed between bottom metal electrode 204 and top metal electrode 202. This second portion of second insulator layer 208 may define the width of the tunnel junction.

The insulating material may be a dielectric, including alumina ($Al_2O_3$), hafnia ($HfO_2$), silicon nitride ($Si_3N_4$), or silicon oxide ($SiO_2$), glass, or quartz. The insulating material may be a metal oxide, including an oxide of an metal described herein. The insulating material may be a low-k dielectric or a high-k dielectric. A low-k dielectric may have a dielectric constant of less than or equal to 4.0, less than or equal to 3.9, less than or equal to 3.5, less than or equal to 3.0, less than or equal to 2.5, less than or equal to 2.0, or less than or equal to 1.5. A high-k dieletric may have a dielectric constant greater than 4.0, greater than or equal to 5.0, greater than or equal to 10, greater than or equal to 20, or greater than or equal to 50. The thickness of the insulating layer serving as the tunneling junction may depend on the material and/or the dielectric constant. For alumina, the thickness can be about 2 nm, which results in a tunneling current of about 100 pA. The thickness may also depend on the molecule to be analyzed. The thickness cannot be too large, otherwise the tunneling current may go through a portion of the molecule larger than the portion of interest (e.g., the tunneling current may pass through multiple nucleotides instead of a single nucleotide). The first insulating material may be the same or different material as the second insulating material. The second insulating material may be a material that adheres to the conducting material. For example, if the conducting material is platinum, the insulating material may be alumina.

The thickness of the insulating layer serving as the tunneling junction (e.g., the thickness of the second insulating material) may be 1 nm or less, from 1 nm to 2 nm, from 2 nm to 3 nm, from 3 nm to 4 nm, from 4 nm to 5 nm, or greater than 5 nm in embodiments. The thickness of the first insulating material may be greater than the thickness of the second insulating material. The thickness of the first insulating material may be from 2 to 5 times thicker, 5 to 10 times thicker, or 10 times to 20 times thicker, including 10 times thicker, than the thickness of the second insulating material. The thickness refers to the height of the material.

A nanopore may be an aperture through the electrodes, the insulating layer, and the substrate. The nanopore may be aperture 212. Second insulator layer 208 may constitute the insulating layer that defines part of aperture 212.

Bottom metal electrode 204, top metal electrode 202, and the insulating layer may define a portion of an aperture. Substrate 210 may also define a portion of an aperture. The total aperture may be defined by substrate 210, bottom metal electrode 204, second insulator layer 208, and top metal electrode 202. Aperture 212 may be cylindrical. If aperture 212 is not cylindrical, aperture 212 may be described by a characteristic dimension. The characteristic dimension may describe a length, a width, a length of a major axis, or a length of a minor axis. The characteristic dimension may be in a plane parallel to that of the substrate. If aperture 212 is not cylindrical, the characteristic dimension may be the diameter of a cylinder having the same volume and the same height as aperture 212. The diameter or the characteristic dimension of the aperture may be from 0.9 nm to 30 nm, including from 0.9 nm to 1.0 nm, 1.0 nm to 1.5 nm, 1.5 nm to 2.0 nm, 2.0 nm to 2.5 nm, 2.5 nm to 5 nm, 5 nm to 10 nm, 10 nm to 15 nm, 15 nm to 20 nm, or 20 nm to 30 nm. In some embodiments, aperture 212 may be a slit. The slit may be similar in shape to a rectangular solid, which may be characterized by a length and width in a plane parallel to that of the substrate.

Bottom metal electrode 204 and top metal electrode 202 may be deposited in an intersecting pattern. However, because the bottom metal electrode 204 and top metal electrode 202 are separated by an insulating layer, bottom metal electrode 204 and top metal electrode 202 do not contact each other. Bottom metal electrode 204 may have a first longitudinal axis. The first longitudinal axis may be axis 250. The longitudinal axis may be along the length of bottom metal electrode 204. Bottom metal electrode 204 may be symmetric or substantially symmetric about axis 250. Top metal electrode 202 may have a second longitudinal axis. The second longitudinal axis may be axis 252. Similar to the first longitudinal axis, the second longitudinal axis may be along the length of top metal electrode 202, and top metal electrode 202 may be symmetric or substantially symmetric about axis 252.

A first plane with axis 250 may be orthogonal to the surface of substrate 210. A second plane with axis 252 may be orthogonal to the surface of substrate 210. The first plane and the second plane may intersect at a non-zero angle. The two axes may not be in the same plane because the electrodes are at different heights above the substrate. If the axes were projected onto a plane parallel with the surface of substrate 210, the axes may intersect at the non-zero angle. The non-zero angle may be from 45 degrees to 95 degrees, including from 45 degrees to 55 degrees, from 55 degrees to 65 degrees, from 65 degrees to 75 degrees, from 75 degrees to 85 degrees, from 85 degrees to 95 degrees, or 90 degrees.

The ends of the electrodes may be thicker and wider than the area of the electrode with the aperture. The ends of the electrodes may be contact regions for electrical connections. The area with the aperture may be termed the junction region. The contact region and the junction region may be the regions shown in FIG. 4A and FIG. 4B. The junction region may be within 5 nm, 10 nm, 15 nm, 20 nm, 30 nm, 40 nm, or 50 nm of the center of the aperture. The junction region may the area of the electrode that has a width substantially equal to the width of the electrode at the location of the aperture. A substantially equal width is a width within 5%, 10%, or 15% of another width. The width of the electrode in the junction region may be the minimum width of the electrode. The contact region may include the maximum width of the electrode. The contact region may include any portion of the electrode farther away from the aperture than the location of the maximum width.

The thickness of the electrode may be the height of the electrode. The thickness of the electrode in an area of the electrode may be the maximum, mean average, or median thickness. The thickness of the electrode may be from 2 nm to 5 nm, from 5 nm to 10 nm, or greater than 10 nm. The width of the electrode in an area may be the maximum, mean average, or median width. The width of the electrode may be from 10 nm to 50 nm, from 50 nm to 100 nm, from 100 nm to 200 nm, from 200 nm to 500 nm, or greater than 500 nm.

The system may include a power supply in electrical communication with at least one of the first electrode or the second electrode. A power supply may be power supply 254 in FIG. 2. The power supply may provide a constant voltage or a constant current. The power supply may provide voltages from 0 to 1 V, including from 10 mV to 100 mV, from 100 mV to 200 mV, from 200 mV to 300 mV, from 300 mV to 500 mV, or from 500 mV to 1 V. In some embodiments, the power supply may provide currents of 0 to 30 nA, including from 1 pA to 10 pA, from 10 pA to 100 pA, from 100 pA to 1 nA, 1 nA to 10 nA, or from 10 nA to 30 nA. As examples, power supply 258 may supply a direct current voltage, an alternating current voltage, or a different waveform (e.g., pulse, sine, square, triangle, or sawtooth).

The system may include an electrical meter in electrical communication with at least one of the first electrode or the second electrode. An electrical meter may be meter 256. The electrical meter may be a voltage meter or a current meter.

The system may include a second power supply. The second power supply may be power supply 258. The second power supply may be configured to apply an electric field through the aperture. The second power supply may not be in electrical communication with the first electrode and may not be in electrical communication with the second electrode. The second power supply may be in electrical communication with a third electrode. The third electrode may be electrode 260. In addition, the second power supply may be in electrical communication with a fourth electrode, such as electrode 262. The third electrode and the fourth electrode may be positioned such that a longitudinal axis (e.g., axis 264) through the center of the aperture intersects the third electrode and the fourth electrode.

A single device may refer to the solid state portion of the system or the portion of the system fabricated through semiconductor process techniques. The device may include the first electrode, the second electrode, the insulating layer, and the substrate. The system may include a plurality of devices. The devices may be arranged in an array. The devices may have electrical connections from each pair of electrodes in each device to a plurality of power supplies or a single power supply. The devices may have connections to a plurality of electrical meters. Using a plurality of analysis systems may allow multiplexing. The plurality of devices may include from 50 to 100, from 100 to 500, from 500 to 1,000, from 1,000 to 5,000, from 5,000 to 10,000, or over 10,000 devices.

Additional details of sequencing systems are described in U.S. Patent Publication No. US 2018/0031523A1, filed Jul. 27, 2017, the contents of which are incorporated herein for all purposes.

IV. Method of Manufacturing

Methods of manufacturing devices and systems may include a process to deposit an electrode with non-vertical sidewalls and a process to taper the height and thickness of the electrode.

A. Sloping Sidewalls

As described above, sloping sidewalls can be used to allow an overlying insulator layer to more easily cover the underlying conductive material layer, thereby reducing the likelihood of shorting or flaking.

Figure 5:
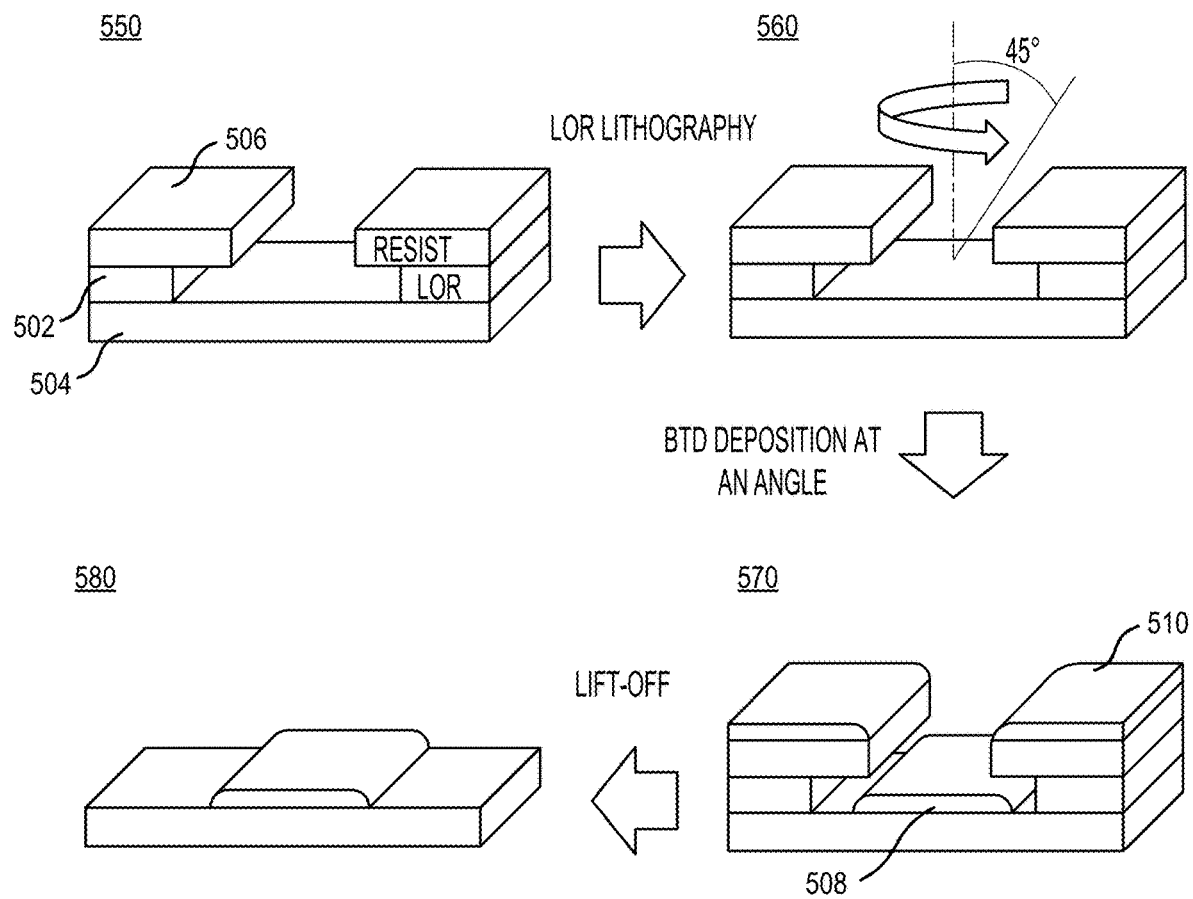
FIG. 5 shows a process flow to deposit an electrode with non-vertical sidewalls according to embodiments of the present invention.

FIG. 5 shows a process flow to deposit an electrode with non-vertical sidewalls. In the first step 550, A lift-off resist 502 is deposited on underlying layer 504. Underlying layer 504 may be the substrate or a previously deposited layer above the substrate. Another resist layer 506 is deposited on top of lift-off resist 502. Resist layer 506 is patterned to expose lift-off resist 502. Lift-off resist 502 is then patterned to create an undercut under resist layer 506 and above underlying layer 504. The undercut may be created by using developer that removes a portion of lift-off resist 502 under resist layer 506. Resist layer 506 overhangs lift-off resist 502. Developer may be a liquid used to remove resist after a portion of the resist has been exposed to light through a patterned mask. The developer may be any suitable developer used in photolithography. Developers may include I-line resists, such as TMAH (Tetramethylammonium hydroxide)-based MIF (metal-ion free) and MIB (metal-ion-bearing) developers. Developers may include AZ 300MIF, MF-24A, M452, among other developers.

As shown in the second step 560 of the process flow in FIG. 5, biased-target deposition at a an 45 degree angle may be used to deposit the metal. Angles may include angles from 30 degrees to 70 degrees, including for example, from 30 degrees to 40 degrees, from 40 degrees to 50 degrees, from 50 degrees to 60 degrees, from 60 degrees to 70 degrees, or 45 degrees. The wafer may be rotated continuously around the vertical axis during the deposition process.

In the third step 570, a metal layer 508 on underlying layer 504 may be deposited. As a result of the overhang in the resist, the angled deposition, and the rotating wafer, the sidewall of metal layer 508 may not be vertical. The sidewalls may be sloping or curved. The metal can be deposited under the overhang of resist layer 506. Biased target deposition may allow for high quality, pinhole-free, ultra-thin layers while avoiding interface mixing.

In the fourth step 580, lift-off resist 502 may be removed or "lifted off," which removes resist layer 506 and metal 510 deposited on top of resist layer 506. Lift-off resist may be removed by an organic solvent, including N-methyl-2-pyrrolidone (NMP). The result may be underlying layer 504 with metal layer 508. Metal layer 508 may be an electrode of a device.

Techniques other than those used in FIG. 5 of forming sloping sidewalls may also be used in embodiments of the present invention. Other techniques include inductively coupled plasma reactive ion etching (ICP RIE), ion milling at an angle, and gray-scale lithography followed by ME.

B. Width and Thickness Tapering

The tapering of the width and thickness of the electrode, as shown in FIGS. 4A and 4B, may also be achieved using lift-off resist.

FIG. 6A shows how different sized openings of resist can lead to different thicknesses and width of a metal layer. A process similar to that shown in FIG. 5 may be used to deposit the metal layer. However, the opening between the resist layer may be varied to vary the width and thickness of the metal layer.

A resist layer 602 and a lift-off resist 604 are deposited and patterned on underlying layer 606. However, in the junction region, the width, $W_3$, of the opening between resist layer 602 is narrower than the corresponding width, $W_4$, in the contact region. The smaller width, $W_3$, may result in a narrower metal layer 608 deposited in the junction region than metal layer 610 deposited in the contact region. Also because less material may be deposited through a narrower opening, the height, $H_3$, of metal layer 608 in the junction region may also be less than height, $H_4$, of metal layer 610 in the contact region.

FIG. 6B shows a top view of how the resist openings may be tapered to achieve the geometry for the electrode shown in FIG. 4B. The opening in resist layer 602 may be monotonically or continuously reduced from width $W_4$ to width $W_3$ along the intended length of the later-deposited metal layer 608. The width of the resist openings may or may not be the same as the width of the electrode that is deposited. For example, $W_4$ may not be the same as $W_2$, and $W_3$ may not be the same as $W_1$. Because the electrode is deposited at an angle, some of the electrode may be formed underneath the overhang in resist layer 602. As a result, the width of the electrode may be wider than the corresponding width of the resist opening. After lift-off resist 604 and resist layer 602 are removed, the geometry shown in FIG. 4B may be achieved.

C. Example Method

Figure 7A:
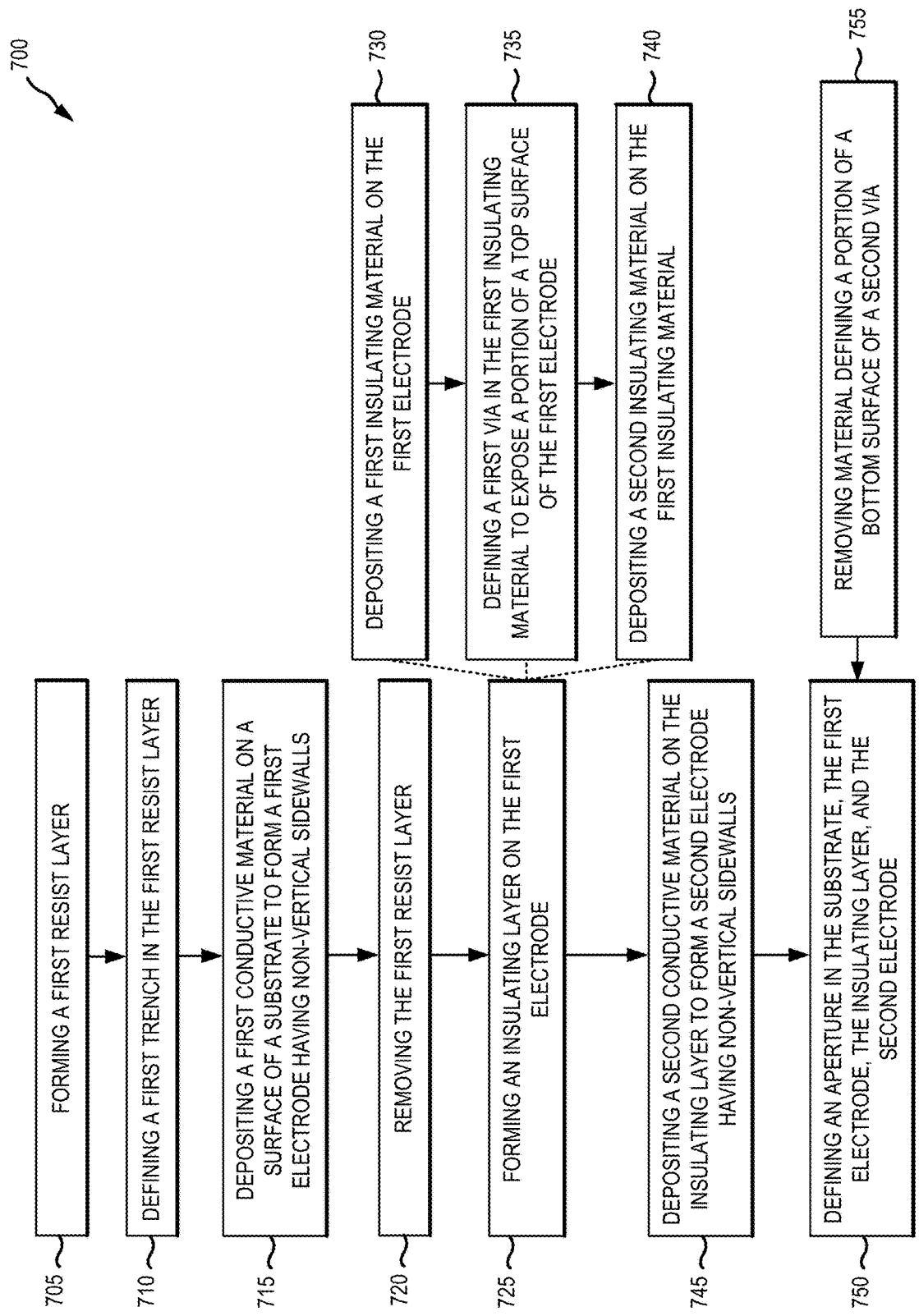
FIG. 7A shows a method of manufacturing a system for analyzing a molecule according to embodiments of the present invention.

FIG. 7A shows a method 700 of manufacturing a system for analyzing a molecule. Method 700 may include electrodes with sloping sidewalls and two insulator layers. In addition, method 700 may also include tapering the electrode in two dimensions so that the electrode is easier to manufacture. Method 700 may be viewed in forming a structure similar to that in FIG. 2. Blocks 705-720 may be for forming bottom metal electrode 204. Blocks 725-740 may be for forming first insulator layer 206 and second insulator layer 208. Block 745 may be for forming top metal electrode 202. Blocks 750 and 755 may be for forming aperture 212.

At block 705, a first resist layer may be formed on a substrate before depositing a first conductive layer. The first resist layer may include two different resist sublayers. A first portion of the first resist layer may be a sublayer underneath a second portion of the first resist layer. The first portion of the first resist layer may be lift-off resist, and the second portion of the first resist layer may be a resist other than lift-off resist. For example, in FIG. 5, the first portion of the first resist layer may be lift-off resist 502 and second portion of the first resist layer may be resist layer 506.

Figure 7B:
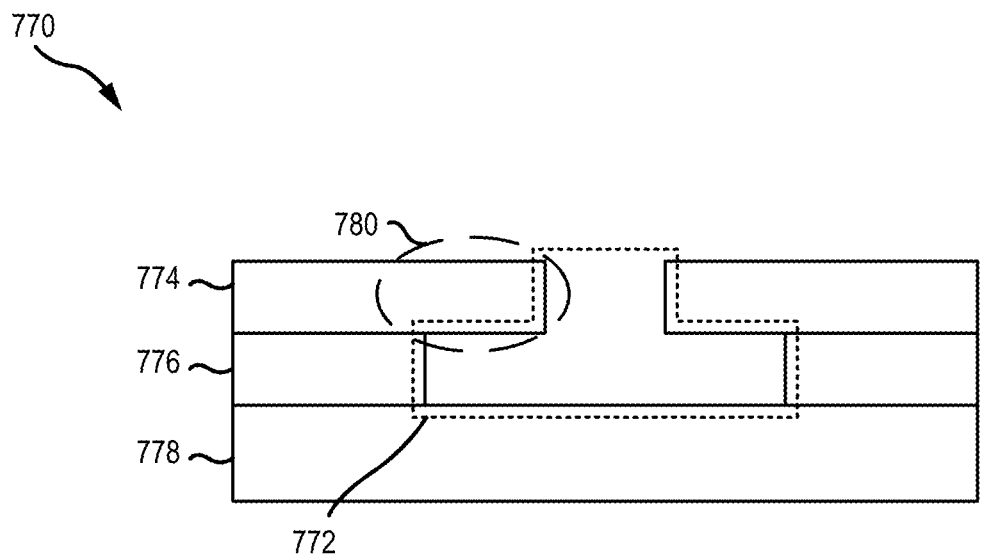
FIGS. 7B and 7C show cross-sections of a trench in a resist layer according to embodiments of the present invention.
Figure 7C:
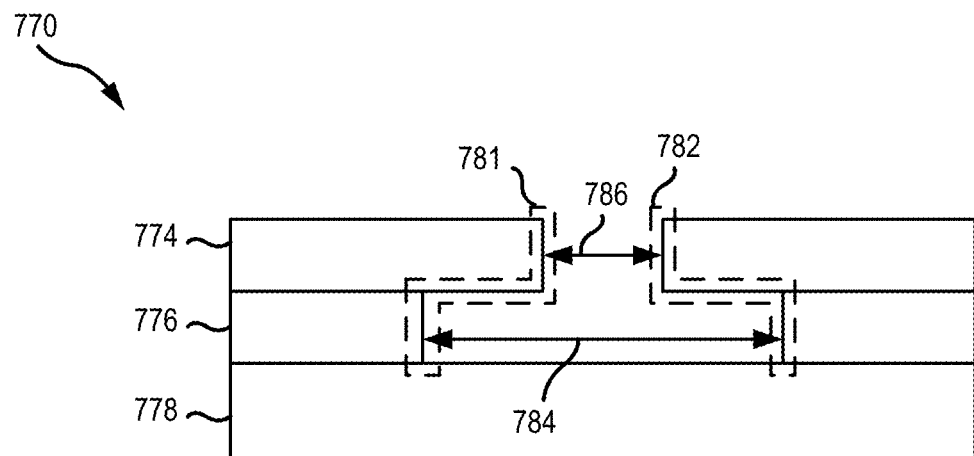

At block 710, a first trench may be defined in the first resist layer. FIGS. 7B and 7C show a possible structure 770 related to block 710. The first trench may be first trench 772. The first resist layer may include top portion 774 and bottom portion 776. Top portion 774 may be a resist layer, similar to resist layer 506 in FIG. 5, and bottom portion 776 may be lift-off resist 502. The first resist layer may be on substrate 778. First trench 772 may be defined in part by an overhang 780 of top portion 774 of the first resist layer. First trench 772 may include a first sidewall 781 and a second sidewall 782, with first sidewall 781 opposite or facing second sidewall 782. First sidewall 781 and second sidewall 782 may be the sidewalls defining the sides of first trench 772. These sidewalls may not be completely vertical throughout because of the overhang. First sidewall 781 may include the top portion 774 of the first resist layer and bottom portion 776 of the first resist layer. Second sidewall 782 may also include top portion 774 of the first resist layer and bottom portion 776 of the first resist layer.

The width at the top of first trench 772 may be narrower than at the bottom of first trench 772 because the top portion 774 of the first resist layer overhangs past the bottom portion 776 of the first resist layer. A first width 784 of the first trench 772 may be defined by a distance from first sidewall 781 having bottom portion 776 to second sidewall 782 having bottom portion 776. A second width 786 of first trench 772 may be defined by a distance from first sidewall 781 having top portion 774 to second sidewall 782 having top portion 774. First width 784 is greater than second width 786. First width 784 and second width 786 may be measured on a plane orthogonal to the trench and orthogonal to the substrate. The two portions of the trench may be patterned by any suitable photolithography method. Bottom portion 776 of the first resist layer may be patterned with a wet chemical (e.g., developer) that removes bottom portion 776 of first trench 772 faster than top portion 774 of the first resist layer.

The width of the trench at the top of the trench may vary along the length of the trench. A wider trench may result in a wider first electrode. The trench may terminate at two ends along the length of the trench. The width at the top of the trench may taper to a narrower width from an end to the center of the trench. The trench may be similar to the resist opening shown in FIG. 6B. A narrower width at the top of the trench may result in a narrower width in the deposited first electrode. A region of the first electrode with the narrower width may be the junction area of a device, where the aperture may be later defined. The junction area may be the area where the first electrode and the second electrode overlap.

At block 715, a first conductive material may be deposited on a surface of a substrate to form a first electrode having non-vertical sidewalls. Depositing the first conductive material may include depositing the first conductive material at a non-perpendicular angle while rotating the substrate. The non-perpendicular angle may be from 30 degrees to 60 degrees, including from 40 to 50 degrees and at 45 degrees. The first conductive material may be deposited by biased target deposition. The first conductive material may be any conductive material or any metal described herein.

As a result of the trench described in blocks 705-715 and angled deposition, the first electrode having non-vertical sidewalls may be formed through deposition alone without a need to etch the deposited first conductive material.

At block 720, the first resist layer may be removed after depositing the first conductive layer. The first resist layer includes bottom portion 776 and top portion 774. The first resist layer may be removed with an organic solvent. After the removal of the resist, the first electrode may remain on the substrate.

At block 725, an insulating layer may be formed on the first electrode. The insulating material may be any insulating material, e.g., as described herein. The insulating layer may be sufficiently thick such that there is no or little tunneling current between the electrodes.

Block 725 may performed using the steps of blocks 730-740 in embodiments. At block 730, to form the insulating layer, a first insulating material may be deposited as a first insulator layer on the first electrode. As examples, the first insulating material may be deposited by ion beam deposition (IBD) or atomic layer deposition (ALD). The first insulating material may be any insulating material described herein.

At block 735, a first via in the first insulating material may be defined to expose a portion of a top surface of the first electrode. The first via may be defined by patterning using electron beam lithography and wet etching the first insulating material. The portion of the top surface of the first electrode may be defined by a wet etch of the insulating material. A wet etch may be used because a dry etch may sputter metal material, increasing the possibility of a short.

At block 740, a second insulating material may be deposited as a second insulator layer on the first insulating material. The second insulating material may be any insulating material or dielectric described herein. The second insulating material may be deposited on a surface of the first via to define a second via. The second via may as a result have smaller dimensions than the first via. At the bottom of the first via, the second insulating material may contact the top surface of the first electrode. The first insulating material may have a thickness greater than the second insulating material. The second insulating material may be deposited by atomic layer deposition. The first and second insulating materials may be any insulating material described herein. Multiple insulating layers may reduce the possibility of incomplete coverage and the possibility of flaking.

At block 745, a second conductive material may be deposited on the insulating layer to form a second electrode having non-vertical sidewalls. The second conductive material may be any conductive material or metal described herein. The second electrode may be top metal electrode 202. Depositing the second conductive material may be preceded with forming a second resist layer, where the second resist layer is similar to the first resist layer. The second resist layer may be removed after depositing the second insulating material. The process of forming the second electrode may use steps substantially similar to those used for the first electrode, including blocks 705, 710, 715, and 720.

The second conductive material may be deposited at an orientation at a non-zero angle relative to the first conductive metal. The first electrode may have a first longitudinal axis. The second electrode may have a second longitudinal axis. A first plane may include the first longitudinal axis and may be orthogonal to the surface of the substrate. A second plane may include the second longitudinal axis and may be orthogonal to the surface of the substrate. The first plane and the second plane may intersect at a non-zero degree angle. The non-zero degree angle may be from 85 to 95 degrees, including 90 degrees. The second conductive material may be deposited by biased target deposition while rotating the substrate. The first electrode and the second electrode may overlap in an area at which at least one of the first electrode or the second electrode is at a minimum width after a taper in one direction along the length of the respective electrode or a taper toward the center of the respective electrode.

At block 750, an aperture may be defined in the substrate, the first electrode, the insulating layer, and the second electrode. The aperture may be aperture 212 in FIG. 2, which may be a nanopore. Defining the aperture may include removing a portion of the second conductive material.

At block 755, material defining a portion of the bottom surface of the second via may be removed. Removing the bottom of the second via may contribute to defining the aperture. The bottom surface of the second via may include the second insulating material but may exclude the first insulating material. After the bottom surface of the second via is removed, a portion of the first electrode may be removed. A portion of the substrate may also be removed. The aperture may extend through the thickness of the substrate. The aperture may have a smaller diameter or characteristic dimension than the second via.

Method 700 may further include connecting at least one of the first electrode or the second electrode to a power supply (e.g., power supply 254). The method may also include connecting at least one of the first electrode or the second electrode to an electrical meter. The power supply may be any power supply described herein. The electrical meter may be any electrical meter described herein. The power supply and/or the electrical meter may be connected to be in communication with a computer system.

V. Method of Analyzing Molecules

Figure 8:
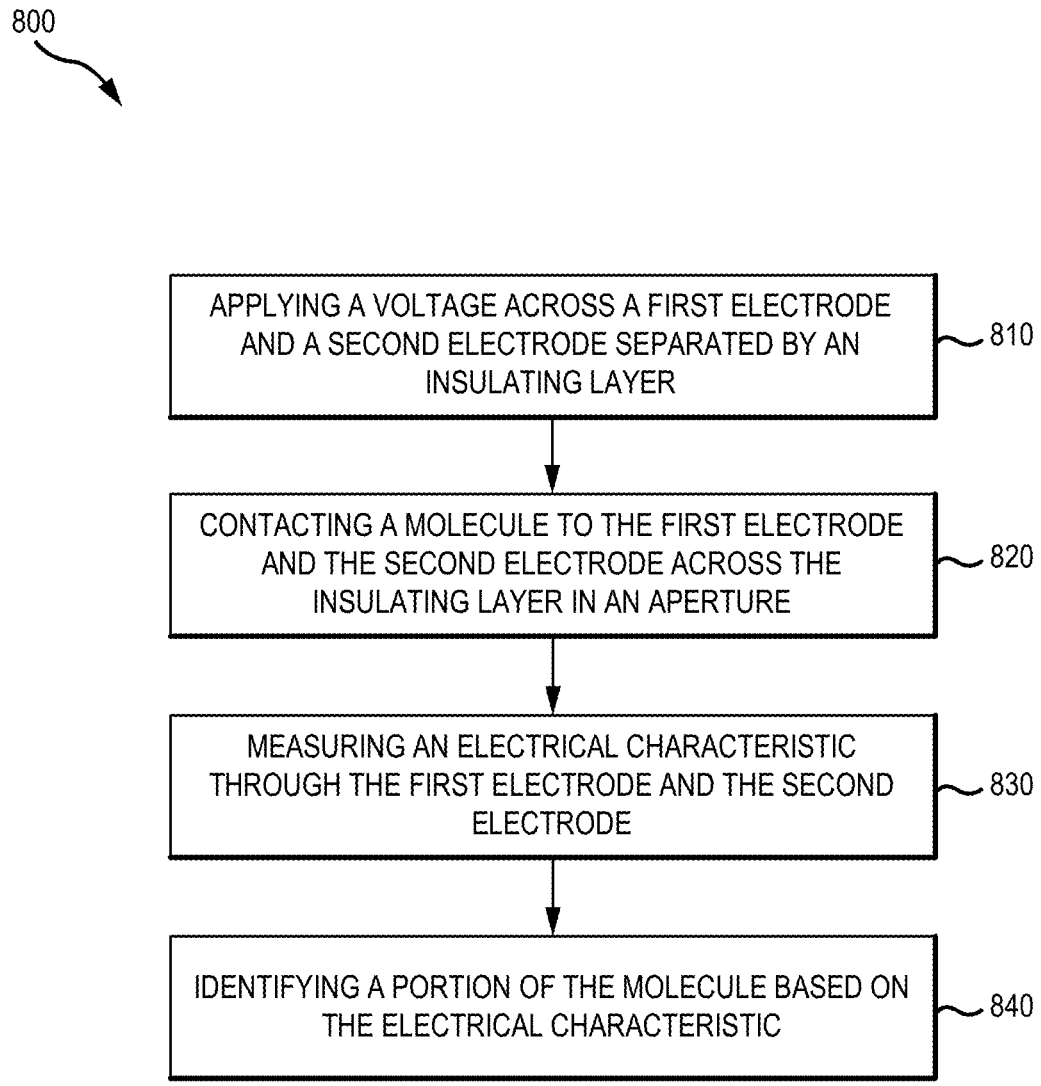
FIG. 8 shows a method of analyzing a molecule according to embodiments of the present invention.

FIG. 8 shows a method 800 of analyzing a molecule. Method 800 may use any system or device described herein.

At block 810, voltage may be applied across a first electrode and a second electrode separated by an insulating layer. The insulating layer may include a first insulating material and a second insulating material. The second insulating material may be disposed between the first insulating material and the second electrode. The first insulating material may have a thickness greater than the thickness of the second insulating material. A power supply, including a voltage source, may apply the voltage. The power supply may be controlled by a computer system. The first electrode, second electrode, and insulating layer may be any described herein.

Method 800 may include moving the molecule to the first electrode and the second electrode by electrophoresis or a pressure-driven flow. Electrophoresis may be induced by applying a voltage across a second pair of electrodes as described herein. A pressure-driven flow may be by a pump, impeller, or other suitable instrument. Movement of the molecule may be controlled in part by a computer, through control of electrodes or the pump or impeller.

At block 820, a molecule may be contacted to the first electrode and the second electrode across the insulating layer in an aperture. The first electrode may have non-vertical sidewalls. The second electrode may have non-vertical sidewalls. The insulating layer may be disposed between the first electrode and the second electrode. A portion of the aperture may be defined by the first insulating material and the second insulating material.

The molecule may be a nucleic acid molecule or any biological polymer molecule. For example, a protein may be analyzed to determine the amino acids in the protein.

The first electrode may have a first longitudinal axis. The first electrode may be centered around the first longitudinal axis. The second electrode may have a second longitudinal axis. The second electrode may be centered around the second longitudinal axis. A first plane may include the first longitudinal axis and may be orthogonal to the surface of the substrate. A second plane may include the second longitudinal axis and may be orthogonal to the surface of the substrate. The first plane and the second plane may intersect at a non-zero degree angle, which may be any described herein.

At block 830, an electrical characteristic through the first electrode and the second electrode may be measured. The electrical characteristic may be current, voltage, or resistance. The measurement of the electrical characteristic may include measuring at least one of the amplitude, pulse width, and frequency. The pulse width may also be considered a dwell time, which may be related to the duration of a certain portion of the nucleic acid molecule remaining in contact with both electrodes. In some embodiments, the electrical characteristic may be transformed by a mathematical operation, such as a Fourier transform, and the transform may be analyzed. In embodiments, the measured electrical characteristic may be compared to the applied voltage and adjusted to isolate the oscillation of the nucleic acid molecule.

A change in electrical characteristic may be determined relative to a background electrical characteristic. The electrical characteristic may be measured by an electrical meter, which may take various forms, as will be appreciated by one skilled in the art. Electrical characteristics include current, voltage, and any other characteristic described herein. The measurement may be received by a computer system.

At block 840, a portion of the molecule may be identified based on the electrical characteristic. The electrical characteristic may be compared to a calibration electrical characteristic. For example, the current may be compared to a calibration current measured from a known molecule or portion of a molecule. For example, nucleotides or sequences may have a current pattern that serves as a fingerprint to identify the nucleotide or sequence. The amplitude, frequency, and/or pulse width of the measured current may be used to identify the unknown nucleotide or sequence based on a known nucleotide or sequence. The amplitude may depend on the individual nucleotide and the resistance of the nucleotide. The frequency may depend on how the nucleotide and/or neighboring nucleotides oscillate in the aperture.

A pattern may be recognized and matched to a known nucleotide or sequence. An exact match may not be needed. Instead, if a current measured from an unknown nucleotide or sequence has a certain threshold level of amplitude, frequency, and/or pulse width, the nucleotide or sequence may be identified. Analyzing the current characteristics may be similar to analyzing electrical characteristics from resonant-tunneling diodes. Tunneling recognition of nucleotides may be similar to tunneling recognition of amino acids as described by Zhao et al., "Single-molecule spectroscopy of amino acids and peptides by recognition tunneling," *Nature Nanotech.* 9, (2014) 466-73, the contents of which are incorporated herein by reference for all purposes.

Identifying a portion of the molecule may include identifying the presence or absence of a part of a sequence of the molecule (e.g., a nucleotide or an amino acid) or a functional group. Identifying the portion of the molecule may include comparing the measured electrical characteristic or change in electrical characteristic against a reference value or a calibration value. The electrical characteristic may be current, voltage, or any characteristic described herein. For example, each of the four nucleotides of DNA or each of the 20 amino acids of proteins may have a current or change in current previously characterized. The four nucleotides or 20 amino acids may be a predetermined set from which the portion of the molecule is identified. Distinguishing different portions of the molecule may use current differences on the order of tens of picoamps. The calibration current or reference current may be based on a plurality of readings. For example, the reference current may be based on hundreds, thousands, or tens of thousands of current measurements across the device or similar devices. Such measured values can be averaged, and the average can be compared to a reference or calibration value. Other statistical values besides a mean average can be used, e.g., a median or mode. Identification of the portion of the molecule may use a computer system. The computer system may have reference currents or other electrical characteristics stored within the system.

Method 800 may include repeating the steps with a second sequencing device, e.g., as part of an array of devices. The array of devices may be any array described above. Repeated electrical characteristic measurements of the molecule may improve statistics for the readings and may facilitate identification of the molecule or a portion of the molecule. Method 800 may include contacting the molecule to a plurality of devices. The plurality may include from 50 to 100, from 100 to 500, from 500 to 1,000, from 1,000 to 5,000, from 5,000 to 10,000, or over 10,000 devices. A statistical test may be used to determine if the electrical characteristic distribution from a portion of the molecule is the same or different from reference electrical characteristic.

Additional details of analyzing molecules are described in U.S. patent application Ser. No. 15/610,186, filed May 31, 2017, the contents of which are incorporated herein for all purposes.

VI. Examples

Tunneling junctions were fabricated and tested for current and voltage characteristics. The current and voltage characteristics indicated the presence of a tunneling current.

Figure 9A:
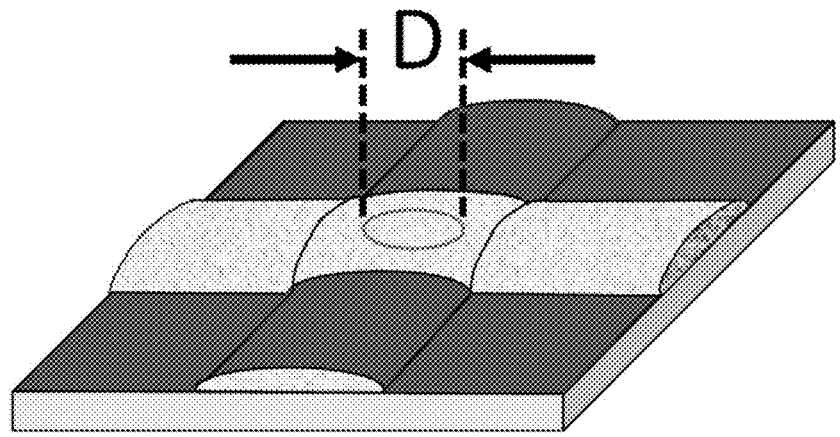
FIG. 9A shows the configuration of a device tested according to embodiments of the present invention.

FIG. 9A shows the configuration of a device tested. The configuration is simplified for illustrative purposes. The devices tested have non-vertical sidewalls. The device resembles the device in step 380 of FIG. 3A, where a tunneling junction is formed by a bottom electrode, an insulator, and a top electrode. However, no hole is etched through any of the layers. The diameter "D" denotes the width of the contact via (e.g., contact via 308) etched in another insulator material.

Figure 9B:
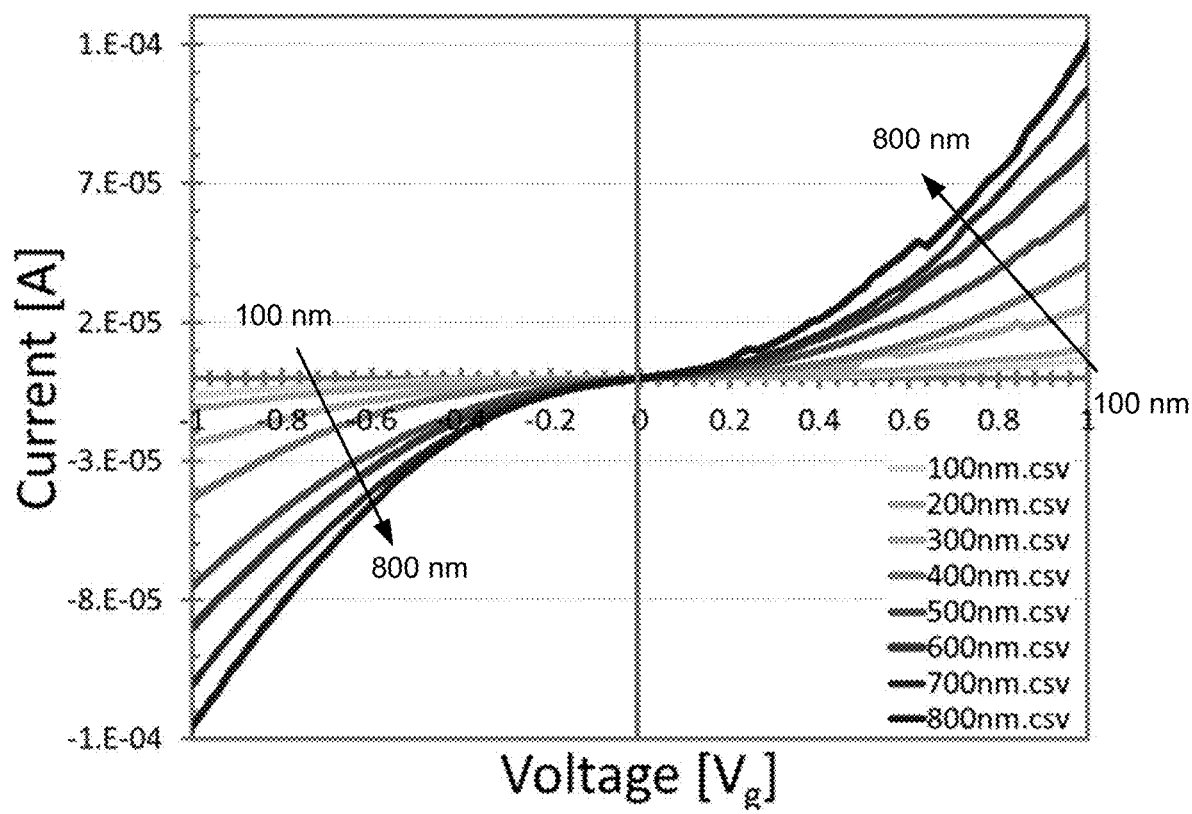
FIG. 9B shows the current-voltage curves for different diameters according to embodiments of the present invention.

FIG. 9B shows the current-voltage curves for different diameters of the contact via. Current through the tunneling junction is shown on the y-axis, and the voltage between the two electrodes is shown on the x-axis. Voltage is applied between the insulator and the top electrodes. The current through the insulator and the electrodes is measured for voltages from −1 V to 1 V. The current is expected to be proportional to the area of the via. Accordingly, a higher current is expected for a larger diameter of the via ("D" in FIG. 9A). The graph shows increasing current as the diameter increases from 100 nm to 800 nm. The graph shows that the device behaves as expected for a tunneling junction.

Figure 9C:
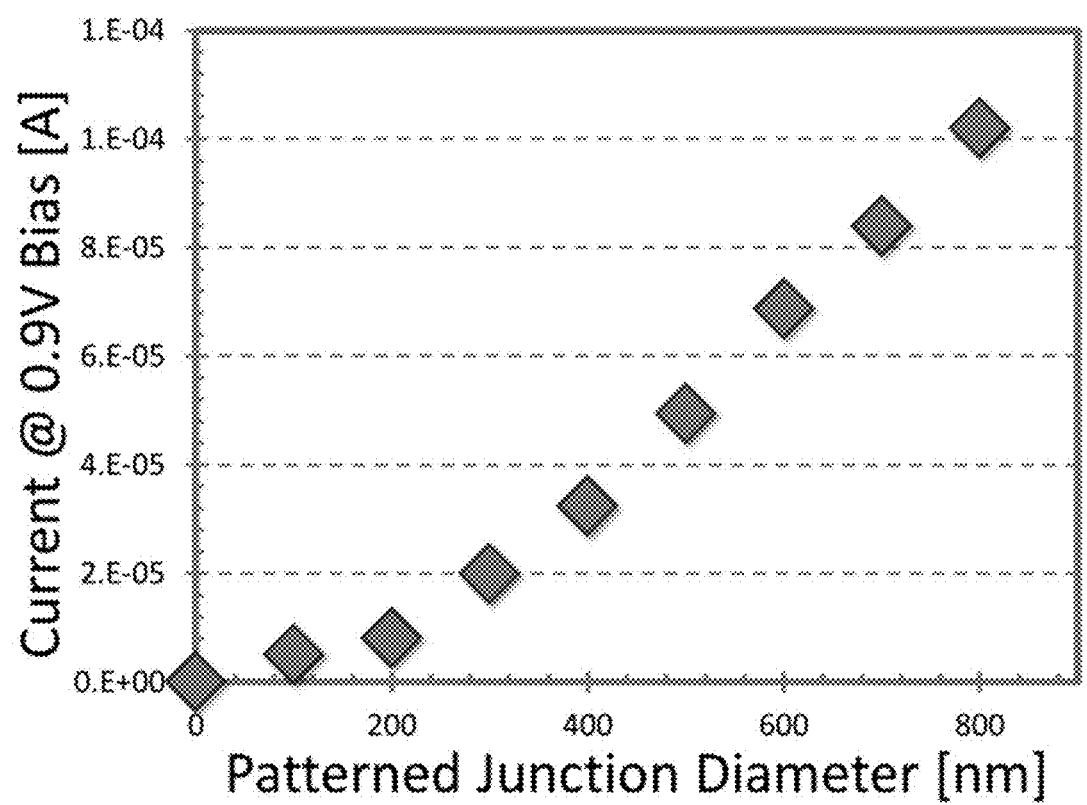
FIG. 9C shows current at a constant voltage for different diameters according to embodiments of the present invention.

FIG. 9C shows the current at 0.9 V bias versus the junction diameter (i.e., contact via diameter). Current is shown on the y-axis. The patterned junction diameter, which is "D" in FIG. 9A, is shown on the x-axis. The current for a constant voltage of 0.9 V to the top electrode is plotted for devices with different diameters. The graph shows a quadratic dependence of current on junction diameter, which is expected because current is proportional to the area of the via, and the area of the via is proportional to the square of the diameter.

Figure 10A:
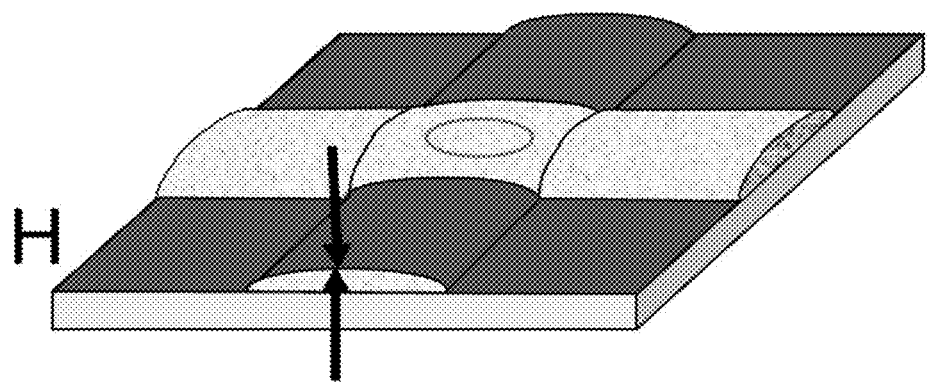
FIG. 10A shows the configuration of a device tested according to embodiments of the present invention.

FIG. 10A shows the configuration of a device tested. The configuration is the same as FIG. 9A. The device is characterized for the thickness "H" of the insulator between the electrodes. This thickness is the thickness of the insulator deposited after the contact via is etched and is the thinnest amount of insulator between the two electrodes.

Figure 10B:
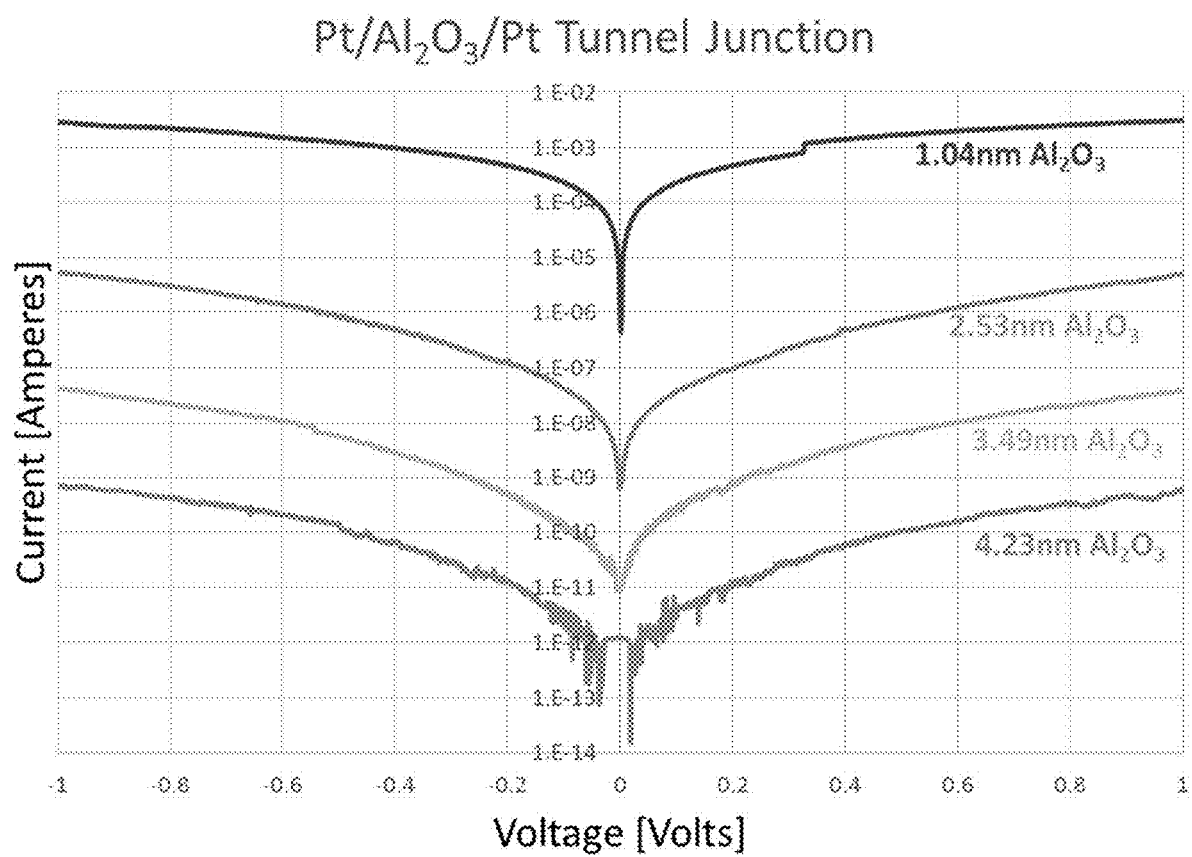
FIG. 10B shows the current-voltage characteristics for different thicknesses of the insulator according to embodiments of the present invention.

FIG. 10B shows the current-voltage characteristics for different thicknesses of the insulator ($Al_2O_3$). The absolute value of current is shown on the y-axis. Voltage applied between the top and bottom electrodes is shown on the x-axis. No voltage is applied to the bottom electrode. The tunneling junction includes two platinum electrodes sandwiching an aluminum oxide dielectric. The different curves show the current and voltage for different thicknesses (i.e., "H" in FIG. 10A) of the aluminum oxide dielectric between the electrodes. A thicker insulator results in lower current, as expected.

Out of 126 junctions tested, 124 showed current-voltage characteristics that indicated a tunneling diode. Two junctions showed an ohmic response, indicating a short. These testing results show that high yield of tunneling junctions can be achieved.

Figure 11:
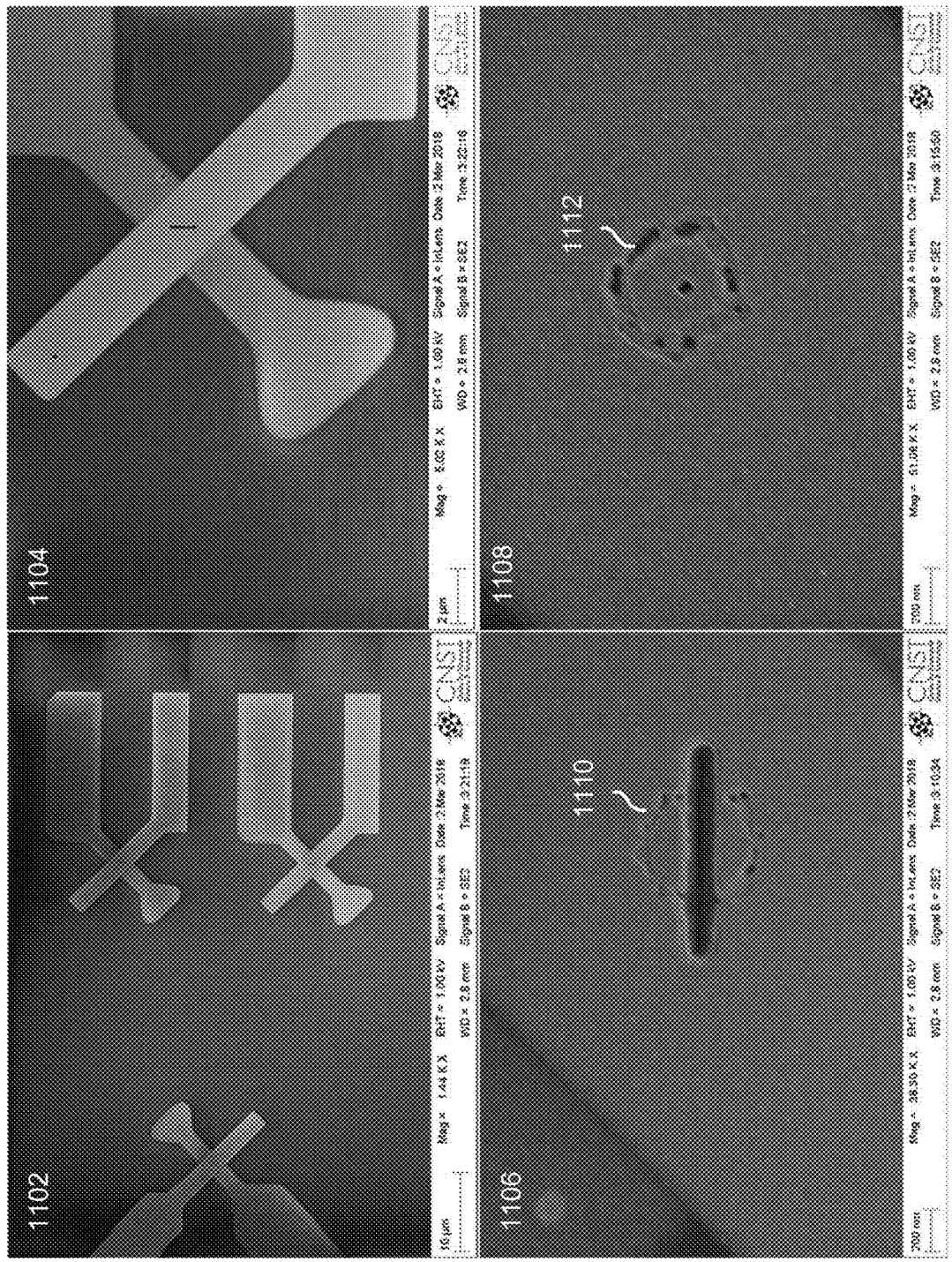
FIG. 11 shows SEM images of tunneling junction devices according to embodiments of the present invention.

FIG. 11 shows scanning electron microscope images of tunneling junction devices. Panel 1102 shows the electrodes of three junction devices. Panel 1104 shows a more magnified image of a single junction device. Panel 1106 shows an image of a nanoslit defined in a junction device. Panel 1108 shows an image of a nanopore defined in a junction device. Circles 1110 and 1112 show the topography of the contact via etched. These images show that an aperture (a slit or a pore) can be etched inside the contact via.

VII. Computer System

Figure 12:
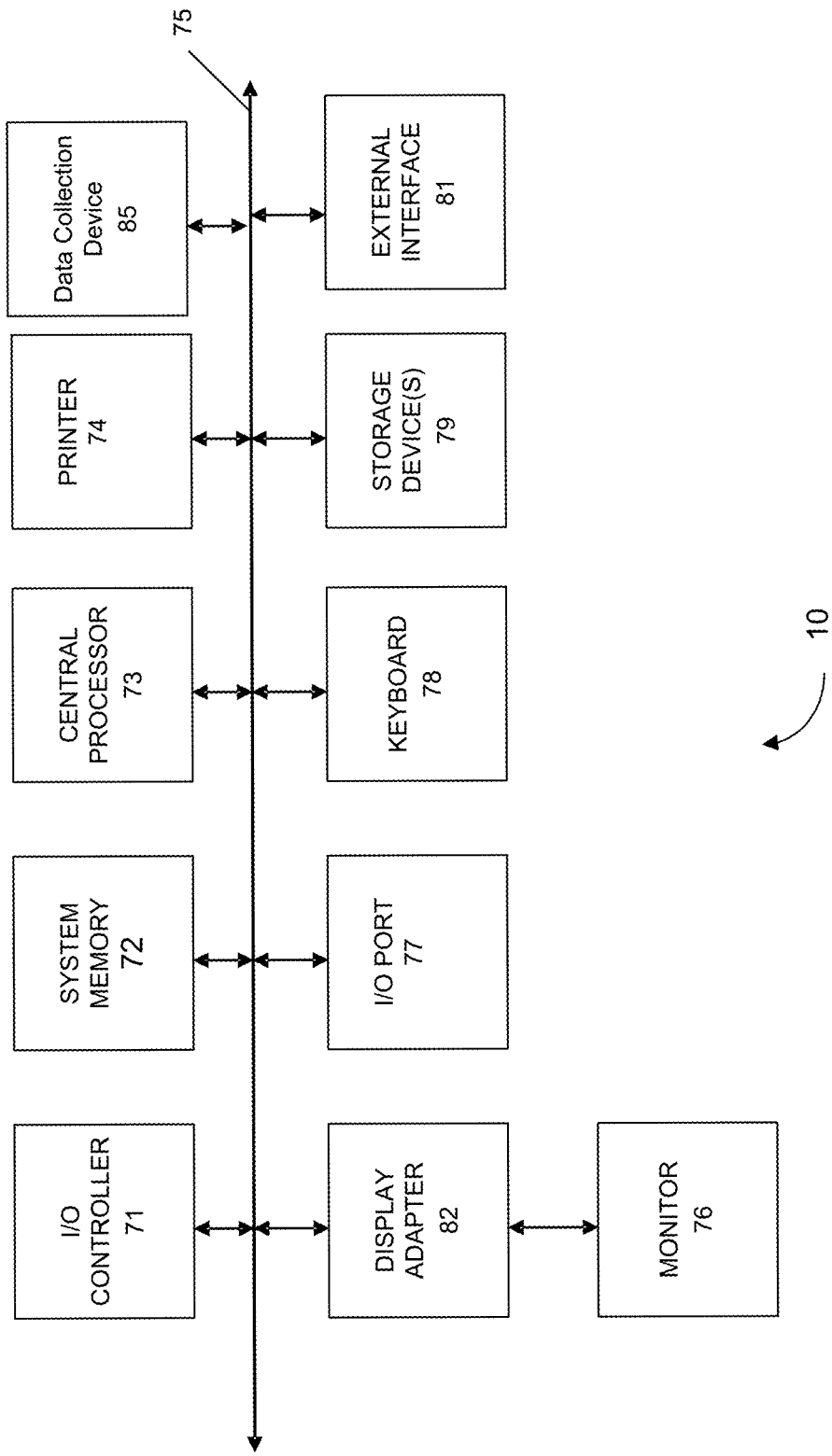
FIG. 12 shows a computer system according to embodiments of the present invention.

Any of the computer systems mentioned herein may utilize any suitable number of subsystems. Examples of such subsystems are shown in FIG. 12 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 12 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®, Thunderbolt). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

Figure 13:
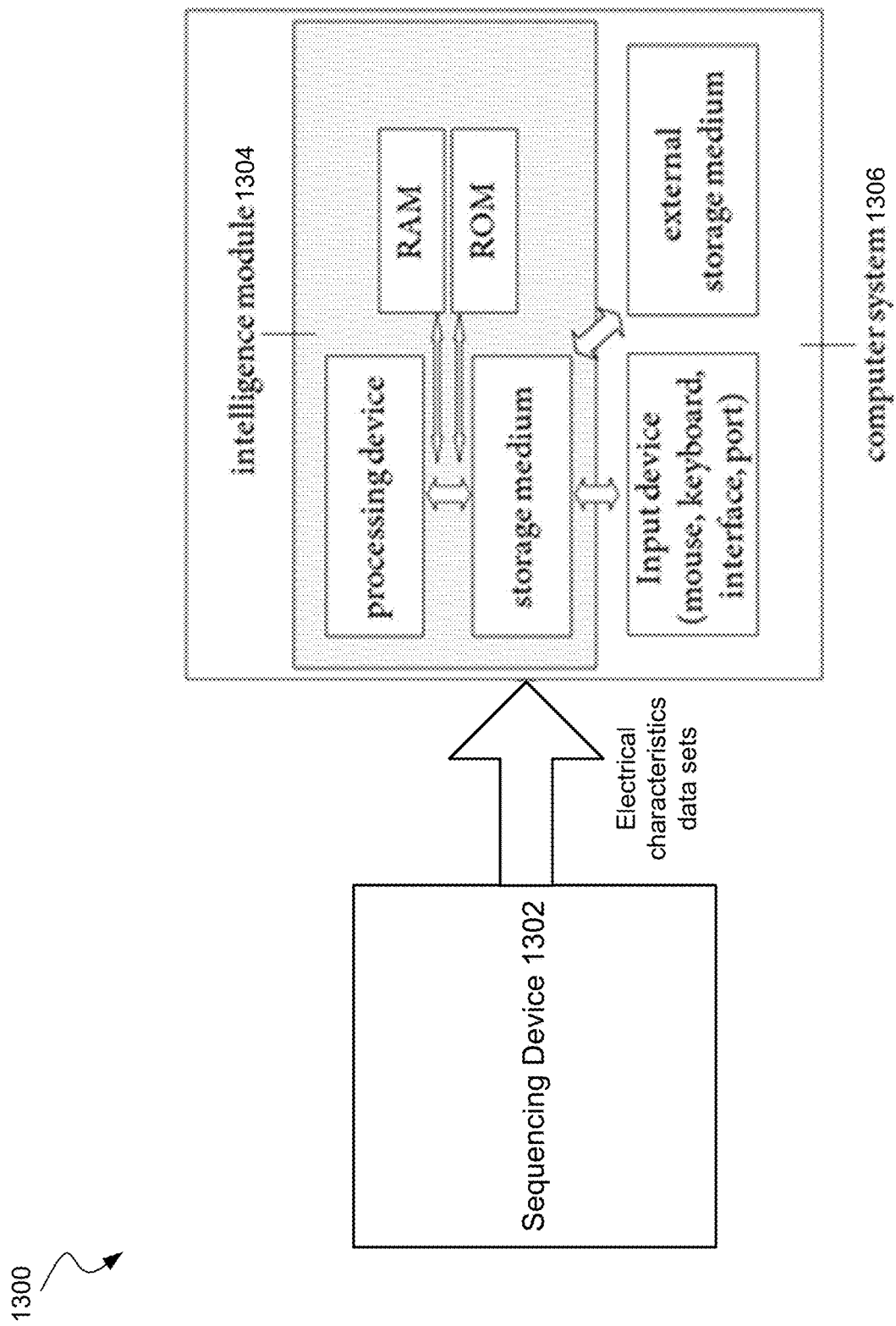
FIG. 13 shows an analysis system according to embodiments of the present invention.

FIG. 13 shows an exemplary analysis system. The system depicted in FIG. 13 comprises a sequencing device 1302 and an intelligence module 1304 that is part of the computer system 1306. Sequencing device 1302 may include system 200 or any system described herein. Applying a voltage across electrodes (e.g., block 810 in FIG. 8), contacting a molecule to electrodes (e.g., block 820 in FIG. 8), and/or measuring the electrical characteristic through the electrodes (e.g., block 830 in FIG. 8) may be performed by sequencing device 1302. Computer system 1306 may include parts or all of computer system 10. In some embodiments, computer system 1306 may measure the electrical characteristic through the electrodes (e.g., block 830 in FIG. 8). For example, raw analog or digital output signals may be converted to a current or voltage by computer system 1306. Computer system 1306 may identify a portion of the molecule based on the electrical characteristic (e.g., block 840 in FIG. 8). The data sets (electrical characteristics data sets) are transferred from the sequencing device 1302 to the intelligence module 1304 or vice versa via a network connection or a direct connection. The data sets may for example be processed to identify nucleotides. The identification steps may be implemented by software stored on the hardware of computer system 1306. The data sets may be processed by computer code running on the processor and being stored on the storage device of the intelligence module and after processing transferred back to the storage device of the sequencing device, where the modified data may be displayed on a displaying device. In some embodiments, the intelligence module may also be implemented in the sequencing device.

Figure 14:
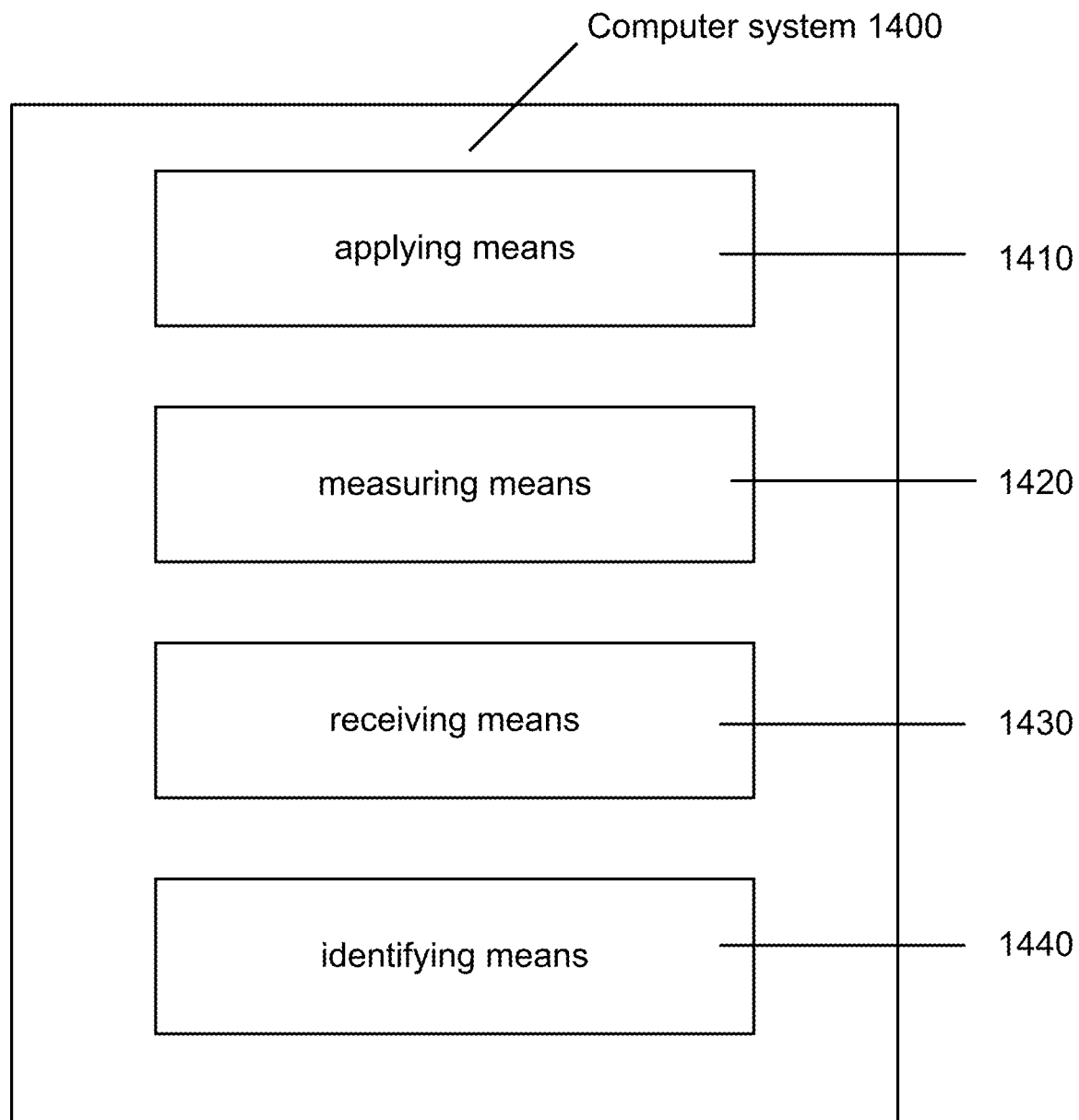
FIG. 14 shows a computer system according to embodiments of the present invention.

FIG. 14 shows that computer system 1400 may comprise applying means 1410, which may include, for example, applying a voltage across a first electrode and a second electrode separated by an insulating layer (e.g., block 810 of FIG. 8). Computer system 1400 may send an instruction to a sequencing device (e.g., sequencing device 1302 of FIG. 13) to apply a voltage across electrodes. Computer system 1400 may be a field-programmable gate array (FPGA) or application-specific integrated circuit (ASIC) computer. Computer system 1400 may also include measuring means 1420, which may include measuring an electrical characteristic through the first electrode and the second electrode (e.g., block 820 of FIG. 8). Computer system 1400 may further include receiving means, which may include receiving electrical characteristic data from a sequencing system (e.g., block 830 of FIG. 8). Computer system 1400 may also include identifying means, which may include, for example, identifying a portion of the molecule based on the electrical characteristic (e.g., block 840 of FIG. 8).

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the molecule" includes reference to one or more molecules and equivalents thereof known to those skilled in the art, and so forth. The invention has now been described in detail for the purposes of clarity and understanding. However, it will be appreciated that certain changes and modifications may be practice within the scope of the appended claims.

All publications, patents, and patent applications cited herein are hereby incorporated by reference in their entirety for all purposes. None is admitted to be prior art.

What is claimed is:

1. A method of manufacturing a system for analyzing a molecule, the method comprising:
    depositing a first conductive material on a surface of a substrate to form a first electrode having non-vertical sidewalls, the first electrode having a first longitudinal axis, wherein a first plane comprises the first longitudinal axis and is orthogonal to the surface of the substrate;
    forming an insulating layer on the first electrode;
    depositing a second conductive material on the insulating layer to form a second electrode having non-vertical sidewalls, the second electrode having a second longitudinal axis, wherein a second plane comprises the second longitudinal axis and is orthogonal to the surface of the substrate, and wherein the first plane and the second plane intersect at a non-zero degree angle; and
    defining an aperture in the substrate, the first electrode, the insulating layer, and the second electrode.

2. The method of claim 1, wherein forming the insulating layer comprises:
    depositing a first insulating material to a first thickness on the first electrode,
    defining a first via in the first insulating material to expose a portion of a top surface of the first electrode,
    depositing a second insulating material to a second thickness on the first insulating material, the second thickness being less than the first thickness,
    depositing the second insulating material on the portion of the top surface of the first electrode to define a second via,
    wherein:
        defining the aperture comprises removing material defining a portion of a bottom surface of the second via, and
        the aperture is defined in the second insulating material and not the first insulating material.

3. The method of claim 2, wherein:
    depositing the first conductive material is by biased target deposition, and
    defining the first via comprises patterning using electron beam lithography and wet etching the first insulating material.

4. The method of claim 1, wherein the non-zero degree angle is from 85 to 95 degrees.

5. The method of claim 1, further comprising:
    forming a first resist layer before depositing the first conductive material,
    defining a first trench in the first resist layer, the first trench having a first width at the bottom of the first trench and a second width at the top of the first trench, the first width being greater than the second width,
    removing the first resist layer after depositing the first conductive material,
    wherein:
        depositing the first conductive material comprises depositing the first conductive material at a non-perpendicular angle while rotating the substrate.

6. The method of claim 5, wherein the non-perpendicular angle is from 40 to 50 degrees.

7. The method of claim 5, wherein:
    the first width decreases from an end of the first trench along the first longitudinal axis, and
    the second width decreases from the end of the first trench along the first longitudinal axis.

8. The method of claim 1, wherein the first electrode tapers in width and thickness from an end of the first electrode along the first longitudinal axis.

9. The method of claim 1, further comprising:
    forming a first resist layer before depositing the second conductive material,
    defining a first trench in the first resist layer, the first trench having a first width at the bottom of the first trench and a second width at the top of the first trench, the first width being greater than the second width,
    removing the first resist layer after depositing the second conductive material,
    wherein:
        depositing the second conductive material comprises depositing the second conductive material at a non-perpendicular angle while rotating the substrate.

10. The method of claim 1, further comprising:
connecting at least one of the first electrode or the second electrode to a power supply, and
connecting at least one of the first electrode or the second electrode to an electrical meter.

\* \* \* \* \*